US010842655B2

United States Patent
Shahriari

(10) Patent No.: US 10,842,655 B2
(45) Date of Patent: Nov. 24, 2020

(54) DEVICE FOR ENDOVASCULAR AORTIC REPAIR AND METHOD OF USING THE SAME

(71) Applicant: Aortic Innovations, LLC, Boca Raton, FL (US)

(72) Inventor: Ali Shahriari, Boca Raton, FL (US)

(73) Assignee: Aortic Innovations, LLC, Boca Raton, FL (US)

( * ) Notice: Subject to any disclaimer, the term of this patent is extended or adjusted under 35 U.S.C. 154(b) by 0 days.

(21) Appl. No.: 16/736,879

(22) Filed: Jan. 8, 2020

(65) Prior Publication Data
US 2020/0138607 A1 May 7, 2020

Related U.S. Application Data

(60) Continuation of application No. 16/042,286, filed on Jul. 23, 2018, now Pat. No. 10,555,823, which is a
(Continued)

(51) Int. Cl.
*A61F 2/856* (2013.01)
*A61F 2/07* (2013.01)
(Continued)

(52) U.S. Cl.
CPC ............... *A61F 2/856* (2013.01); *A61F 2/07* (2013.01); *A61F 2/2418* (2013.01); *A61F 2/82* (2013.01);
(Continued)

(58) Field of Classification Search
CPC .... A61F 2/2418; A61F 2/2412; A61F 2/2436; A61F 2/2433; A61F 2/2475; A61F 2/07; A61F 2/82; A61F 2/89; A61F 2/962
See application file for complete search history.

(56) References Cited

U.S. PATENT DOCUMENTS

| 5,061,275 A | 10/1991 | Wallsten et al. |
| 5,102,417 A | 4/1992 | Palmaz |

(Continued)

FOREIGN PATENT DOCUMENTS

| CN | 102014805 A | 4/2011 |
| DE | 19857887 | 7/2000 |

(Continued)

OTHER PUBLICATIONS

Intentus Group, Intellectual Property Search Services, Two-Part Arterial Stent with Seal, Mar. 1, 2020, pp. 1-19.
(Continued)

*Primary Examiner* — Christopher D. Prone
*Assistant Examiner* — Tiffany P Shipmon
(74) *Attorney, Agent, or Firm* — NK Patent Law

(57) ABSTRACT

An intraluminal vascular prosthesis assembly, having a hollow cylindrical body with a first end and a second end is provided. The assembly includes, at its first end, a first vascular prosthesis portion, and at its second end, a second vascular prosthesis portion which has only a prosthesis material. The vascular prosthesis assembly has a stent portion which is provided between the first vascular prosthesis portion and the second vascular prosthesis portion, the stent portion being free of prosthesis material to allow fluid flow there through and received within the aortic arch and spanning the brachiocephalic artery, left common carotid artery, and left subclavian artery when placed within the aortic arch of a patient.

21 Claims, 19 Drawing Sheets

Related U.S. Application Data continuation of application No. 14/614,628, filed on Feb. 5, 2015, now Pat. No. 10,028,848, which is a continuation of application No. 14/569,306, filed on Dec. 12, 2014, now Pat. No. 9,339,399, which is a division of application No. 13/706,896, filed on Dec. 6, 2012, now Pat. No. 8,940,040.

(60) Provisional application No. 61/723,446, filed on Nov. 7, 2012, provisional application No. 61/567,458, filed on Dec. 6, 2011.

(51) Int. Cl.
*A61F 2/962* (2013.01)
*A61F 2/24* (2006.01)
*A61F 2/82* (2013.01)
*A61F 2/06* (2013.01)
*A61F 2/89* (2013.01)
*A61F 2/90* (2013.01)

(52) U.S. Cl.
CPC ............ *A61F 2/962* (2013.01); *A61F 2/89* (2013.01); *A61F 2/90* (2013.01); *A61F 2002/061* (2013.01); *A61F 2002/067* (2013.01); *A61F 2210/00* (2013.01); *A61F 2210/0014* (2013.01); *A61F 2210/0057* (2013.01); *A61F 2220/0008* (2013.01); *A61F 2220/0016* (2013.01); *A61F 2220/0025* (2013.01); *A61F 2220/0058* (2013.01); *A61F 2220/0075* (2013.01); *A61F 2230/001* (2013.01); *A61F 2230/0034* (2013.01); *A61F 2230/0067* (2013.01); *A61F 2250/0048* (2013.01)

(56) References Cited

U.S. PATENT DOCUMENTS

| | | |
|---|---|---|
| 5,397,355 A | 3/1995 | Martin et al. |
| 5,609,627 A | 3/1997 | Goicoechea et al. |
| 5,716,393 A | 2/1998 | Lindberg et al. |
| 5,718,159 A | 2/1998 | Thompson |
| 5,957,974 A | 9/1999 | Thompson et al. |
| 5,976,179 A | 11/1999 | Inoue |
| 6,004,346 A | 12/1999 | Wolff et al. |
| 6,254,632 B1 | 7/2001 | Wu et al. |
| 6,258,117 B1 | 7/2001 | Camrud et al. |
| 6,334,868 B1 | 1/2002 | Ham |
| 6,464,721 B1 | 10/2002 | Marcade et al. |
| 6,482,228 B1 | 11/2002 | Norred |
| 6,582,462 B1 | 6/2003 | Andersen et al. |
| 6,752,829 B2 | 6/2004 | Kocur et al. |
| 6,773,457 B2 | 8/2004 | Ivancev et al. |
| 6,814,752 B1 | 11/2004 | Chuter |
| 6,918,925 B2 | 7/2005 | Tehrani |
| 7,018,404 B2 | 3/2006 | Holmberg et al. |
| 7,074,235 B1 | 7/2006 | Roy |
| 7,252,682 B2 | 8/2007 | Seguin |
| 7,294,146 B2 | 11/2007 | Chew et al. |
| 7,306,623 B2 | 12/2007 | Watson |
| 7,393,360 B2 | 7/2008 | Spenser et al. |
| 7,510,574 B2 | 3/2009 | Le et al. |
| 7,588,597 B2 | 9/2009 | Frid |
| 7,771,467 B2 | 8/2010 | Svensson |
| 7,780,726 B2 | 8/2010 | Seguin |
| 7,799,072 B2 | 9/2010 | Greenberg |
| 7,914,569 B2 | 3/2011 | Nguyen et al. |
| 7,947,074 B2 | 5/2011 | Meretei |
| 7,998,187 B2 | 8/2011 | Hartley et al. |
| 8,002,816 B2 | 8/2011 | Greenberg |
| 8,002,826 B2 | 8/2011 | Seguin |
| 8,016,877 B2 | 9/2011 | Seguin et al. |
| 8,021,408 B2 | 9/2011 | Kang et al. |
| 8,025,694 B2 | 9/2011 | Strauss et al. |
| 8,206,438 B2 | 6/2012 | Yang et al. |
| 8,226,710 B2 | 7/2012 | Nguyen et al. |
| 8,394,119 B2 | 3/2013 | Zaver et al. |
| 8,398,701 B2 | 3/2013 | Berez et al. |
| 8,414,635 B2 | 4/2013 | Hyodoh et al. |
| 8,419,788 B2 | 4/2013 | Sheldon et al. |
| 8,425,584 B2 | 4/2013 | Cully et al. |
| 8,506,622 B2 | 8/2013 | Bruszewski et al. |
| 8,545,549 B2 | 10/2013 | Hartley et al. |
| 8,562,673 B2 | 10/2013 | Yeung et al. |
| 8,603,156 B2 | 12/2013 | Hartley et al. |
| 8,617,234 B2 | 12/2013 | Garcia et al. |
| 8,623,067 B2 | 1/2014 | Berez et al. |
| 8,652,198 B2 | 2/2014 | Andreas et al. |
| 8,715,317 B1 | 5/2014 | Janardhan et al. |
| 8,715,337 B2 | 5/2014 | Chuter |
| 8,721,676 B1 | 5/2014 | Janardhan et al. |
| 8,864,808 B2 | 10/2014 | Greenberg et al. |
| 8,911,490 B2 | 12/2014 | Perkins et al. |
| 8,940,040 B2 | 1/2015 | Shahriari |
| 9,005,270 B2 | 4/2015 | Perkins et al. |
| 9,034,007 B2 | 5/2015 | Janardhan |
| 9,095,343 B2 | 8/2015 | Berez et al. |
| 9,114,001 B2 | 8/2015 | Kusleika et al. |
| 9,157,174 B2 | 10/2015 | Kusleika |
| 9,179,931 B2 | 11/2015 | Janardhan et al. |
| 9,220,613 B2 | 12/2015 | Amault De La Menardiere et al. |
| 9,220,899 B2 | 12/2015 | Cattaneo et al. |
| 9,269,739 B2 | 2/2016 | Mollard et al. |
| 9,289,282 B2 | 3/2016 | Olson et al. |
| 9,314,324 B2 | 4/2016 | Janardhan et al. |
| 9,358,140 B1 | 6/2016 | Connor et al. |
| 9,393,021 B2 | 7/2016 | Garcia et al. |
| 9,393,136 B2 | 7/2016 | Perkins et al. |
| 9,452,070 B2 | 9/2016 | Kusleika |
| 9,561,102 B2 | 2/2017 | Rust et al. |
| 9,629,739 B2 | 4/2017 | Slazas et al. |
| 9,757,263 B2 | 9/2017 | Roeder et al. |
| 9,833,341 B2 | 12/2017 | Bogenschuetz et al. |
| 9,943,427 B2 | 4/2018 | Losordo et al. |
| 10,028,848 B2 | 7/2018 | Shahriari |
| 10,034,784 B2 | 7/2018 | Tang |
| 10,321,985 B2 | 6/2019 | Barthold et al. |
| 2001/0044650 A1 | 11/2001 | Simso et al. |
| 2002/0082684 A1 | 6/2002 | Mishaly |
| 2002/0177890 A1 | 11/2002 | Lenker |
| 2003/0040771 A1* | 2/2003 | Hyodoh ............ D04C 1/06 606/200 |
| 2004/0210304 A1 | 10/2004 | Seguin et al. |
| 2004/0249399 A1 | 12/2004 | Cinquin et al. |
| 2005/0043790 A1 | 2/2005 | Seguin |
| 2005/0197687 A1 | 9/2005 | Molaei et al. |
| 2006/0149351 A1 | 7/2006 | Smirthwaite et al. |
| 2006/0155366 A1 | 7/2006 | LaDuca et al. |
| 2007/0067014 A1 | 3/2007 | Ke et al. |
| 2007/0095283 A1 | 5/2007 | Galewski |
| 2007/0168013 A1 | 7/2007 | Douglas |
| 2007/0203559 A1 | 8/2007 | Freudenthal |
| 2007/0219613 A1 | 9/2007 | Kao et al. |
| 2007/0250146 A1 | 10/2007 | Cully et al. |
| 2007/0276464 A1 | 11/2007 | Valencia et al. |
| 2008/0132993 A1 | 6/2008 | Rasmussen et al. |
| 2008/0132999 A1 | 6/2008 | Mericle et al. |
| 2008/0262592 A1 | 10/2008 | Jordan et al. |
| 2008/0275548 A1 | 11/2008 | Svensson |
| 2009/0036977 A1 | 2/2009 | Rassat et al. |
| 2009/0099644 A1 | 4/2009 | Biadillah et al. |
| 2009/0099650 A1 | 4/2009 | Bolduc et al. |
| 2009/0125098 A1* | 5/2009 | Chuter ............ A61F 2/95 623/1.26 |
| 2009/0171456 A1 | 7/2009 | Kveen et al. |
| 2009/0198315 A1 | 8/2009 | Boudjemline |
| 2009/0312834 A1 | 12/2009 | Wood et al. |
| 2010/0042202 A1 | 2/2010 | Ramzipoor et al. |
| 2010/0049313 A1 | 2/2010 | Alon et al. |
| 2010/0087907 A1 | 4/2010 | Lattouf |
| 2010/0094409 A1 | 4/2010 | Barker et al. |
| 2011/0257731 A1 | 10/2011 | Hartley et al. |

(56) References Cited

U.S. PATENT DOCUMENTS

| | | |
|---|---|---|
| 2012/0046726 A1 | 2/2012 | Chuter |
| 2012/0089218 A1 | 4/2012 | Dardi |
| 2013/0013050 A1 | 1/2013 | Shalev et al. |
| 2013/0144373 A1 | 6/2013 | Shahriari |
| 2014/0046428 A1 | 2/2014 | Cragg et al. |
| 2014/0172064 A1 | 6/2014 | Kelly |
| 2014/0316513 A1 | 10/2014 | Tang |
| 2014/0336749 A1 | 11/2014 | Bogenschuetz et al. |
| 2016/0022450 A1 | 1/2016 | Hehrlein |
| 2016/0270935 A1 | 9/2016 | Rasmussen et al. |
| 2017/0209254 A1 | 7/2017 | Barthold et al. |

FOREIGN PATENT DOCUMENTS

| | | |
|---|---|---|
| DE | 102014114747 A1 | 4/2016 |
| DE | 10065824 | 10/2018 |
| EP | 2787925 A1 | 10/2014 |
| JP | 2011502628 A | 1/2011 |
| JP | 2011507658 A | 3/2011 |
| WO | 0187180 A2 | 11/2001 |
| WO | 03003949 A2 | 1/2003 |
| WO | 2004089249 A1 | 10/2004 |
| WO | 2005087117 A1 | 9/2005 |
| WO | 2006127412 A1 | 11/2006 |
| WO | 2010006627 A1 | 1/2010 |
| WO | 2010031060 A1 | 3/2010 |
| WO | 2010105195 A2 | 9/2010 |
| WO | 2011035154 A1 | 3/2011 |
| WO | 2013040663 A1 | 3/2013 |
| WO | 2013059596 A1 | 4/2013 |
| WO | 2013086132 A1 | 6/2013 |
| WO | 2014072501 A2 | 5/2014 |
| WO | 2012147675 A1 | 7/2014 |

OTHER PUBLICATIONS

Singh, et al. "A biometric Approach for Designing Stent-Graft Structures: Caterpillar Cuticle as Design Model", Journal of the Mechanical Behavior of Biomedical Materials, vol. 30, Feb. 2014, 3 pages, accessed at www.sciencedirect.com/science/article/pii/S175161611300341X.

ISA/US; International Search Report and Written Opinion for International Patent Application No. PCT/US2012/068165, dated Feb. 15, 2013, 8 pages.

Piazza, et al., "Anatomy of the Aortic Valvar Complex and Its Implications for Transcatheter Implantation of the Aortic Valve", Circulation: Cardiovascular Interventions, Journal of the American Heart Association, 2008, 10 pages.

Stoeckel et al., "A Survey of Stent Designs", NDC, 2002, pp. 137-147.

WIPO; International Preliminary Report on Patentability for International Patent Application No. PCT/US2012/068165, dated Jun. 10, 2014, 7 pages.

CIPO; Office Action for Canadian Patent Application No. 2,858,390 dated Jul. 27, 2015, 3 pages.

CNIPA; Office Action for Chinese Patent Application No. 2012800577516 dated May 6, 2015, 6 pages.

EPO; Extended European Search Report for European Patent Application No. 18153473.6 dated Jul. 23, 2018.

JPO; Japanese Patent Office for Japanese Patent Application No. 2017-078010, dated Feb. 20, 2018.

CIPO; Office Action for Canadian Patent Application No. 2,858,390 dated Aug. 24, 2017.

EPO; Examination Report for European Patent Application No. 12854807.0 dated Sep. 1, 2016.

JPO; Office Action for Japanese Patent Application No. 2018-206631, dated Oct. 23, 2019, 9 pages.

CNIPA; Office Action for Chinese Patent Application No. 201680007062.2 dated Sep. 29, 2018, 15 pages.

EPO; Extended European Search Report for European Patent Application No. 16735541.1 dated Jul. 20, 2018, 8 pages.

EPO; Extended European Search Report in European Patent Application No. 16743828.2 dated Sep. 25, 2018.

USPTO; Non-Final Office Action for U.S. Appl. No. 13/706,896 dated Jul. 18, 2014, 10 pages.

USPTO; Non-Final Office Action for U.S. Appl. No. 14/569,306 dated Feb. 12, 2016, 6 pages.

USPTO; Non-Final Office Action for U.S. Appl. No. 14/614,628 dated Sep. 22, 2017, 8 pages.

USPTO; Non-Final Office Action for U.S. Appl. No. 14/614,628 dated Jun. 6, 2017, 9 pages.

USPTO; Non-Final Office Action for U.S. Appl. No. 14/614,628 dated Mar. 25, 2016, 9 pages.

USPTO; Non-Final Office Action for U.S. Appl. No. 16/042,286 dated Jul. 29, 2019, 5 pages.

Di Bartolomeo, et al., "Frozen elephant trunk surgery using the E-vita open plus prosthesis", Masters of Cardiothoracic Surgery, Annals Cardiothoracic Surgery, 2013, vol. 2. No. 5, pp. 656-659.

* cited by examiner

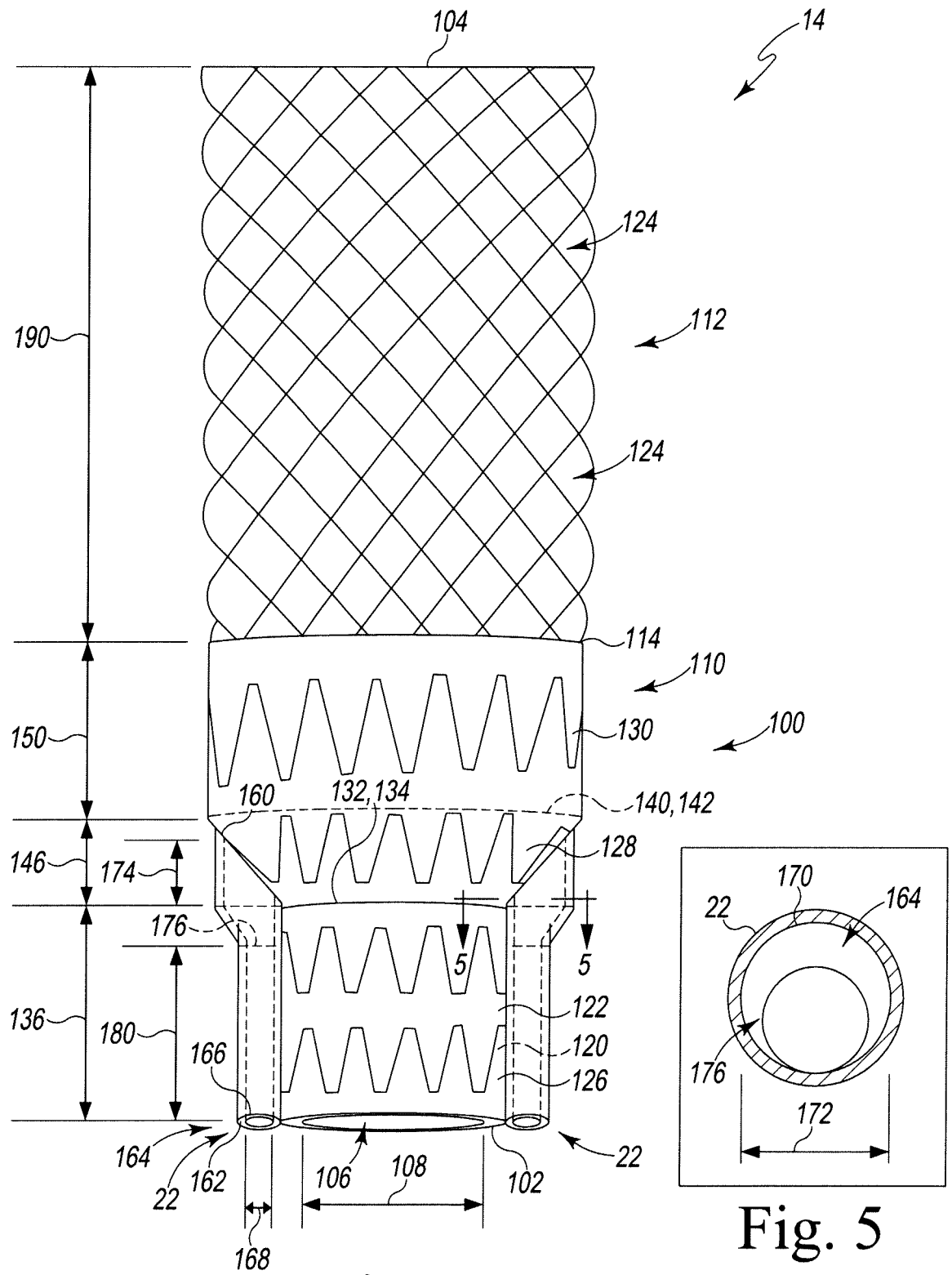

DEVICE FOR ENDOVASCULAR AORTIC REPAIR AND METHOD OF USING THE SAME

This application is a continuation of U.S. patent application Ser. No. 16/042,286 entitled "DEVICE FOR ENDOVASCULAR AORTIC REPAIR AND METHOD OF USING THE SAME," which was filed on Jul. 23, 2018, which is a continuation of U.S. patent application Ser. No. 14/614,628 entitled "Device for Endovascular Aortic Repair and Method of Using the Same," which was filed on Feb. 5, 2015, which is a continuation of U.S. patent application Ser. No. 14/569,306 entitled "Device for Endovascular Aortic Repair and Method of Using the Same," which was filed on Dec. 12, 2014, which is a divisional of U.S. patent application Ser. No. 13/706,896, entitled "Device for Endovascular Aortic Repair and Method of Using the Same," which claims the benefit under 35 U.S.C. § 119 to U.S. Provisional Application Ser. No. 61/567,458 entitled "Transcathetar Aortic Valve for Endovascular Aortic Repair," which was filed on Dec. 6, 2011. Application Ser. No. 13/706,896 also claims priority under § 119 to U.S. Provisional Application Ser. No. 61/723,446 entitled "Transcathetar Aortic Valve for Endovascular Aortic Repair," which was filed on Nov. 7, 2012. Each of the applications referenced herein are incorporated by reference in their entirety.

TECHNICAL FIELD

The present disclosure relates to a device and method of using same for endovascular aortic repair, including repair of aortic valve disease, aortic stenosis, ascending aortic aneurysms, aortic insufficiency, aortic regurgitation, ascending aneurysm, bicuspid valve disease, and/or Type A dissections.

BACKGROUND

The normal aortic root and the ascending aorta are composed of the aortic annulus, the sinuses of Valsalva, the sinutubular junction, and the tubular portion. The challenge facing practitioners of endovascular repair of ascending aortic aneurysms is that there is a very short proximal landing zone at the level of the sinutubular junction, there is variable coronary anatomy from patient to patient, and, in many cases, there is involvement of the aortic valve with either stenosis or insufficiency. Generally speaking, and as discussed in the article SURGERY INSIGHT: THE DILATED ASCENDING AORTA—INDICATIONS FOR SURGICAL INTERVENTION, by James E. Davies and Thralf M. Sundt published in Nature Clinical Practice Cardiovascular Medicine (2007), the contents of which are incorporated herein by reference in its entirety, there are three basic types of involvement of the ascending aorta, designated as Type A, B, or C. These will be discussed in further detail below and are shown in FIGS. 1A-1C, which have been reproduced from the referenced article.

Type A aneurysms are most commonly found in younger patients and patients with connective tissue disorders such as Marfan syndrome. The anatomical characteristics of Type A aneurysms are dilatation of the sinuses of Valsalva with or without dilatation of the aortic annulus. The sinutubular junction is most often dilated. The valve could be normal, stenotic or insufficient. An example of a Type A aneurysm is shown in FIG. 1A.

The anatomical characteristics of Type B aneurysms are dilatation of the tubular portion. Initially the sinutubular junction may be normal or mildly dilated, however as the aneurysm grows, it stretches the sinutubular junction and may eventually lead to aortic insufficiency. The valve could be normal, stenotic or insufficient. The bulk of the aneurysm is at the level of the tubular aorta. An example of a Type B aneurysm is shown in FIG. 1B.

The anatomical characteristics of Type C aneurysms are dilatation of the sinuses of Valsalva, sinutubular junction and the tubular portion of the aorta. The valve could be normal, stenotic or insufficient. Type B and C aneurysms are most commonly found in an older group of patients. An example of a Type C aneurysm is shown in FIG. 1C.

There are devices clinically used for endovascular repair of ascending aortic aneurysms. Although transcatheter valves are a clinical reality, none in clinical use have been designed with the purpose of endovascular repair of multiple types of ascending aortic aneurysms. Indeed, a device is needed that can treat different anatomical variations of ascending aortic aneurysms, create effective proximal and distal seal zones within the aorta, and have a durable valve component, but that also allows for future valve re-interventions. A device is also needed that would allow for treatment of different coronary anatomical variations among the patient population, allow future coronary re-intervention, but that also avoids coronary compression, and enables treatment of possible paravalvular leaks.

SUMMARY

According to one aspect of the disclosure, an endograft device for endovascular repair of ascending aortic aneurysms is disclosed. The endograft device includes a first prosthetic component that has a proximal frame and a distal frame that is secured to the proximal frame and extends to a distal end of the first prosthetic component. The endograft device also includes at least one conduit that is secured to the first prosthetic component and that is positioned adjacent to the proximal frame, and a second prosthetic component that is secured to a proximal end of the first prosthetic component. The second prosthetic component includes a balloon-expandable frame extending distally from a proximal end of the second prosthetic component and a self-expanding frame that is connected to the balloon-expandable frame and extends to a distal end of the second prosthetic component. The endograft device also includes a valve element that is secured to the balloon-expandable frame at the proximal end of the second prosthetic component.

In some embodiments, the self-expanding frame may have an hourglass shape. In some embodiments, the self-expanding frame may include a first section that tapers inwardly between a proximal end and a distal end. The endograft device may also include a second section having a proximal end that is secured to the distal end of the first section. The second section may taper outwardly between the proximal end of the second section and a distal end of the second section. Additionally, in some embodiments, the proximal end of the first section may be connected to a distal end of the balloon-expandable frame.

In some embodiments, the self-expanding frame may include a third section that extends proximally from the proximal end of the first section. The third section may have a passageway defined therein, and the balloon-expandable frame may be positioned in the passageway of the third section of the self-expanding frame. In some embodiments, the balloon-expandable frame may be expandable between an unexpanded position in which an outer surface of the balloon-expandable frame is spaced apart from an inner surface of the self-expanding frame and an expanded position in which the outer surface of the balloon-expandable frame is engaged with the inner surface of the self-expanding frame.

In some embodiments, a plurality of fibers may be attached to the third section of the self-expanding frame. When the balloon-expandable frame is in the expanded position, the outer surface of the balloon-expandable frame may be engaged with the plurality of fibers.

In some embodiments, the proximal frame of the first prosthetic component may have a passageway defined therein, and the distal end of the second prosthetic component may be positioned in the passageway of the first prosthetic component.

In some embodiments, the conduit may include a pair of conduits positioned on opposite sides of the first prosthetic component. Additionally, in some embodiments, the conduit may have a proximal opening that is positioned adjacent to a proximal end of the first prosthetic component.

In some embodiments, the proximal frame may include a first section secured to the distal end of the second prosthetic component, and a second section connected to the first section. The second section may taper outward between a proximal end connected to the first section and a distal end. The conduit may have a distal opening defined in the second section of the proximal frame.

Additionally, in some embodiments, the endograft device may include a stent having a distal end positioned in the proximal opening of the at least one conduit and a proximal end configured to be positioned in a coronary artery.

In some embodiments, an outer surface of the second prosthetic component and an outer surface of the proximal frame of the first prosthetic component may be covered such that fluid is prevented from passing therethrough. Additionally, an outer surface of the distal frame of the first prosthetic component may be uncovered such that is fluid permitted to pass therethrough.

According to another aspect, a transcatheter valve is disclosed. The transcatheter valve includes a frame component having a balloon-expandable frame extending distally from a proximal end of the frame component and a self-expanding frame secured to the balloon-expandable frame. The self-expanding frame includes a first section that tapers inwardly between a proximal end and a distal end, and a second section that tapers outwardly between a proximal end secured to the distal end of the first section and a distal end. A valve element is positioned in the balloon-expandable frame at the proximal end of the frame component.

In some embodiments, the frame component may be a dual-frame component. The self-expanding frame may be an outer frame of the dual-frame component and may have a passageway defined therein. The balloon-expandable frame may be an inner frame of the dual-frame component that is positioned in the passageway defined in the self-expanding frame. Additionally, the balloon-expandable frame may be expandable between an unexpanded position in which an outer surface of the balloon-expandable frame is spaced apart from an inner surface of the self-expanding frame and an expanded position in which the outer surface of the balloon-expandable frame is engaged with the inner surface of the self-expanding frame.

In some embodiments, a plurality of fibers may be attached to the self-expanding frame. When the balloon-expandable frame is in the expanded position, the outer surface of the balloon-expandable frame may be engaged with the plurality of fibers. Additionally, in some embodiments, an outer surface of the first section of the self-expanding frame may be uncovered such that fluid is permitted to pass therethrough and an outer surface of the second section of the self-expanding frame may be covered such that fluid is prevented from passing therethrough.

In some embodiments, the self-expanding frame may include an elongated section extending distally from the second section. The elongated section may have a length that is greater than a combined length of the first section and the second section. Additionally, in some embodiments, the self-expanding frame may be covered with at least one of a collagen and hydrogel. In some embodiments, the valve element may be one of a bicuspid valve and a tricuspid valve.

According to another aspect, a method of repairing a patient's aorta is disclosed. The method includes introducing a first prosthetic component into the patient's aorta such that a proximal frame of the first prosthetic component is positioned in the ascending aorta and a distal frame of the first prosthetic component is positioned in the aortic arch of the patient's aorta, advancing a covered stent through a conduit defined in the first prosthetic component into a coronary artery of the patient's aorta, securing a second prosthetic component to a proximal end of the first prosthetic component in the patient's aorta, and expanding a proximal section of the second prosthetic component into engagement with the aortic annulus of the patient's aorta such that a valve secured to the proximal section is positioned in the aortic annulus proximal to the coronary arteries.

In some embodiments, expanding the proximal section of the second prosthetic component may include operating a balloon-expandable frame. Additionally, in some embodiments, expanding the proximal section of the second prosthetic component may include permitting a self-expanding frame to expand into engagement with the aortic annulus, and operating the balloon-expandable frame may include advancing an outer surface of the balloon-expandable frame into engagement with an inner surface of the self-expanding frame after the self-expanding frame is engaged with the aortic annulus.

In some embodiments, operating the balloon-expandable frame may include advancing an outer surface of the balloon-expandable frame into engagement with the aortic annulus.

In some embodiments, an outer surface of the second prosthetic component and an outer surface of the proximal frame of the first prosthetic component may be covered such that fluid is prevented from passing therethrough. Additionally, an outer surface of the distal frame of the first prosthetic component may be uncovered such that is permitted to pass therethrough.

In some embodiments, introducing the first prosthetic component into the patient's aorta and advancing the covered stent through the conduit defined in the first prosthetic component into the coronary artery of the patient's aorta may be performed during a first surgical procedure. In some embodiments, securing the second prosthetic component to the proximal end of the first prosthetic component and expanding the proximal section of the second prosthetic component into engagement with the aortic annulus of the patient's aorta may be performed during a second surgical procedure different from the first surgical procedure.

In some embodiments, the method may also include introducing the second prosthetic component into the ascending aorta prior to introducing the first prosthetic component.

BRIEF DESCRIPTION OF THE DRAWINGS

Embodiments of the present disclosure will now be described by way of example in greater detail with reference to the attached figures, in which:

FIG. 4 is an elevation view of a distal prosthetic component of the endovascular prosthetic device of FIG. 2;

FIG. 5 is a cross sectional view of the distal prosthetic component of FIG. 4 taken along the line 5-5 in FIG. 4;

DETAILED DESCRIPTION OF THE DRAWINGS

Figure 1:
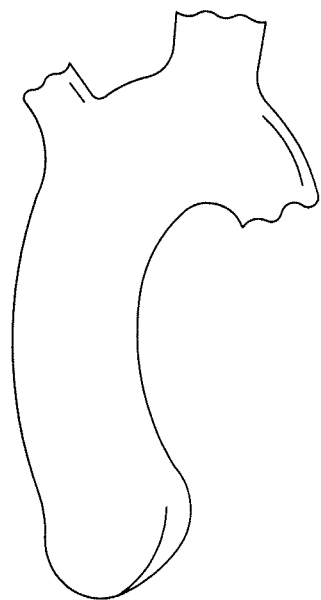
FIG. 1 is an illustrative aorta.
Figure 1B:
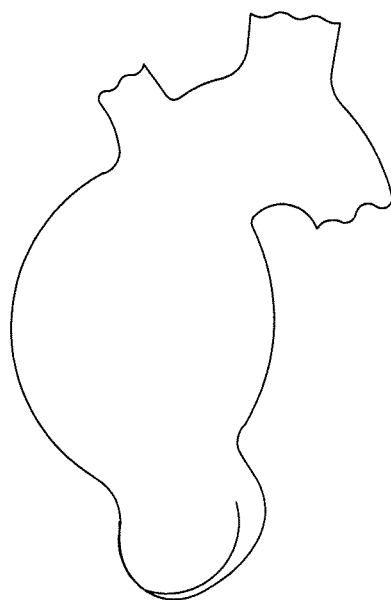
FIG. 1B is an example of a Type B aneurysm.
Figure 1A:
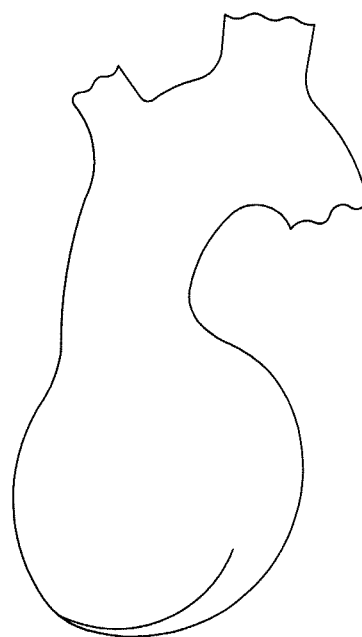
FIG. 1A is an example of a Type A aneurysm.
Figure 1C:
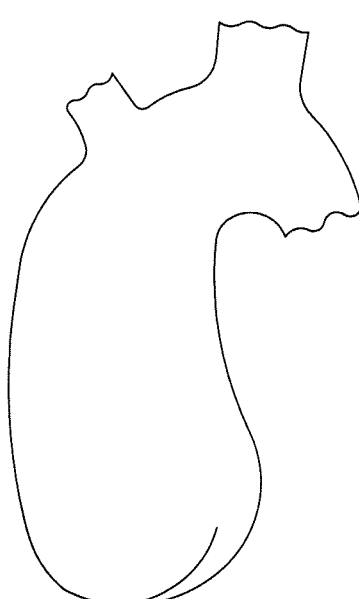
FIG. 1C is an example of a Type C aneurysm.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. For example, the term "proximal" refers to the direction that is generally closest to the heart, and the term "distal" refers to the direction that is generally furthest from the heart.

Referring to FIGS. 2-16, exemplary designs of an endovascular prosthetic device or endograft device 10 (hereinafter device 10) are shown. The device 10 is intended for the treatment of most ascending aortic aneurysms and is configured to treat any type of ascending aneurysm regardless of involvement of the aortic valve and the sinuses of Valsalva. As described in greater detail below, the device 10 permits future coronary and aortic valve interventions as well as extension of a fenestrated/branch graft into the aortic arch. Part of the device 10 may also be modified and used as a transcatheter valve, as described in greater detail below in regard to FIGS. 17-22. Such a valve may be introduced transfemorally or through the subclavian artery or the apex of the heart.

Figure 2:
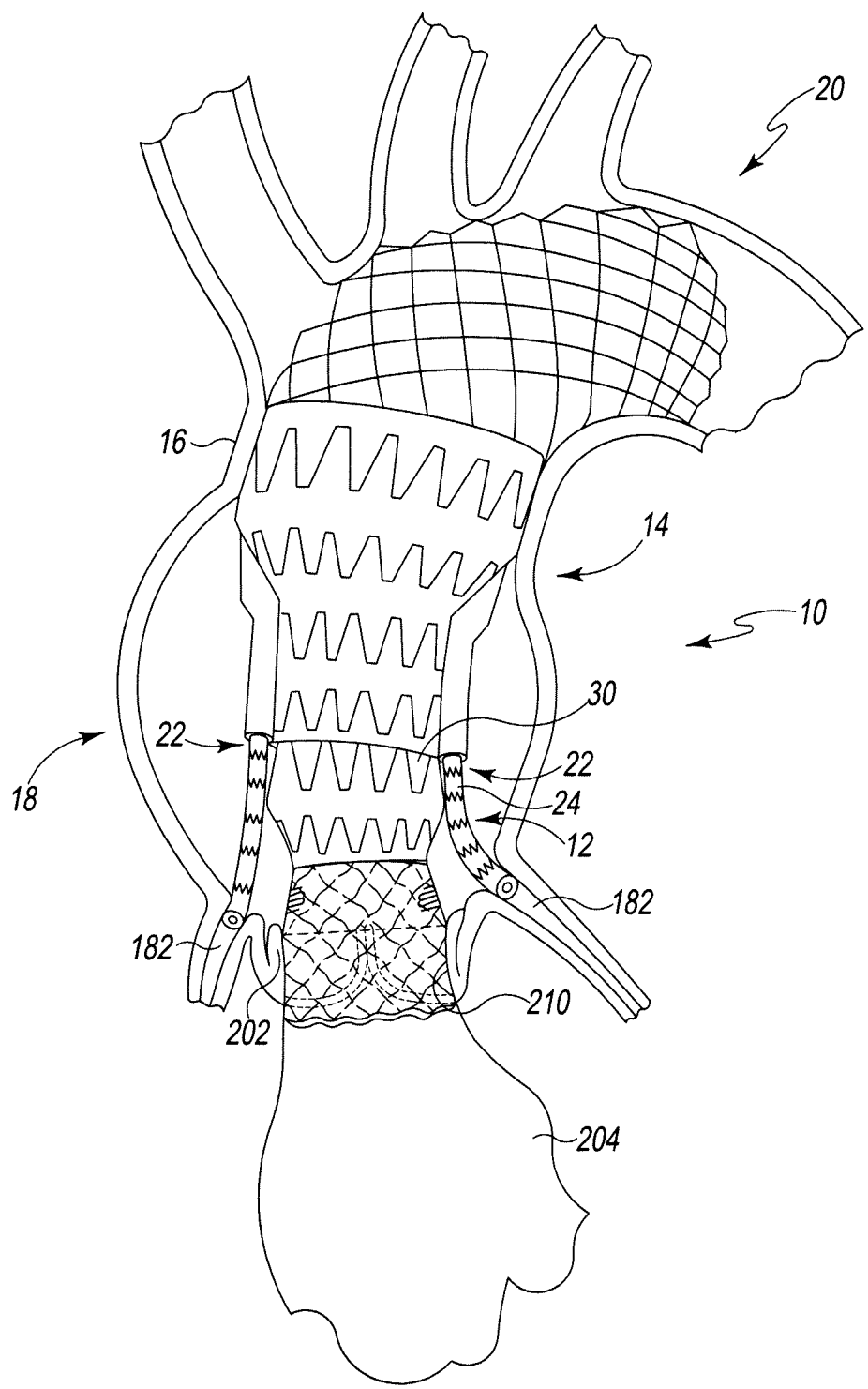
FIG. 2 is partial cutaway view of an aorta with an embodiment of an endovascular prosthetic device implanted therein.

Referring now to FIGS. 2-7, the device 10 includes a proximal component 12 that is attached to a distal component 14. As shown in FIG. 2, the distal component 14 may be secured to the proximal component 12 when implanted into a patient's aorta 16. When implanted, the proximal component 12 is positioned in the patient's ascending aorta 18, while the distal component 14 extends distally into the arch 20 of the patient's aorta 16. The distal component 14 includes a pair of "Endo-cabrol conduits" or conduits 22, and each conduit 22 is sized to receive a catheter or stent 24 for coronary blood flow, as described in greater detail below. The device 10 is configured to treat all ascending aneurysms with or without dilated sinutubular junctions and aortic valve disease.

Figure 3:
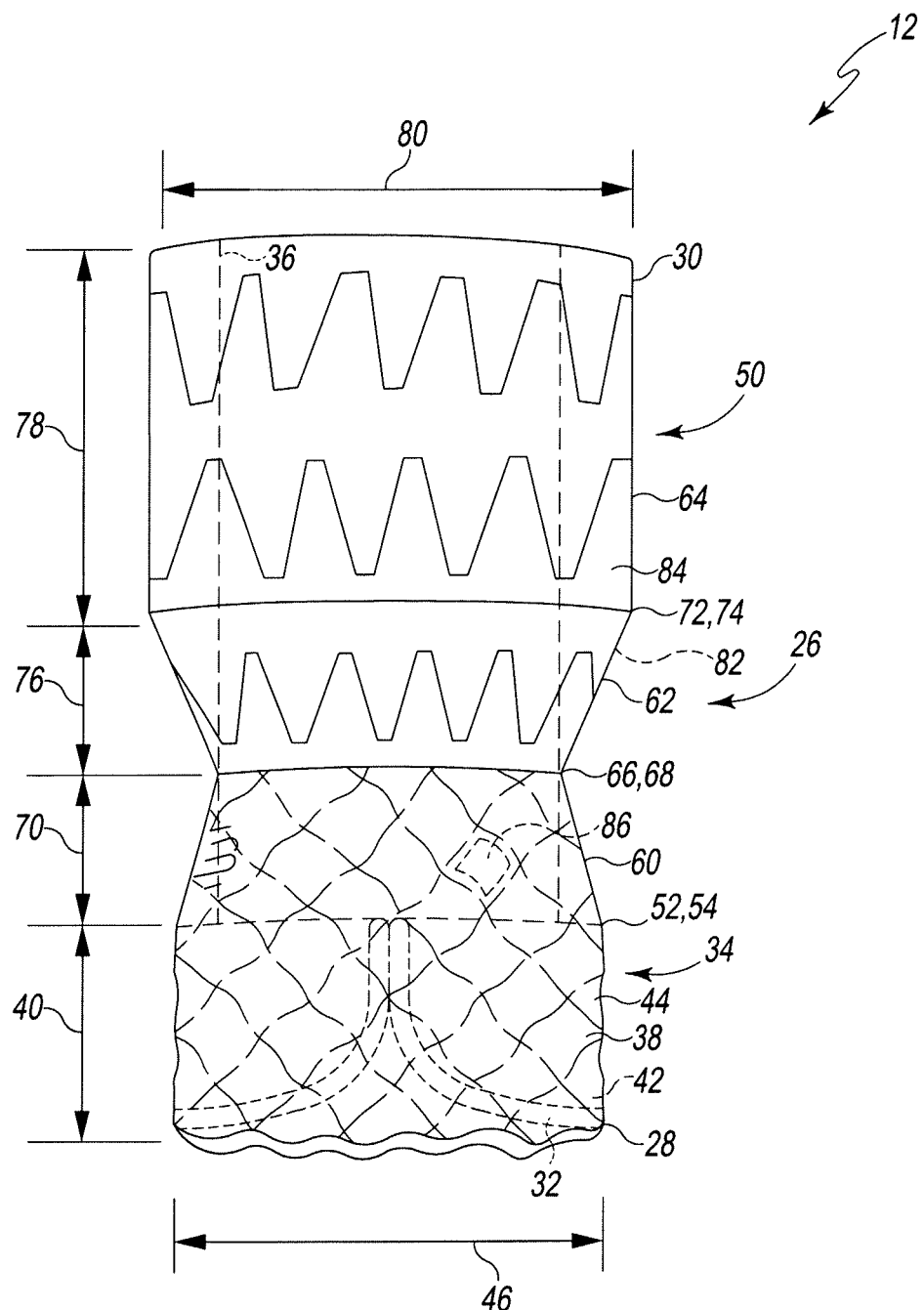
FIG. 3 is an elevation view of a proximal prosthetic component of the endovascular prosthetic device of FIG. 2.

As shown in FIG. 3, the proximal component 12 includes a frame 26 that extends from a proximal end 28 to a distal end 30. The frame 26 is attached to a valve 32 (shown in phantom), which is positioned at the proximal end 28 of the component 12. In the illustrative embodiment, the valve 32 is configured as a bicuspid valve. It should be appreciated that in other embodiments the valve 32 may be tricuspid or quadracuspid. The valve 32 may be constructed from treated bovine pericardium or other suitable proven biological or synthetic material. When the proximal component 12 is implanted into the patient's aorta 16, the valve 32 replaces the aortic valve and permits fluid (i.e., blood) to selectively pass from the heart and into a passageway 36 extending through the proximal component 12.

The valve 32 is housed in a balloon-expandable frame 34 of the frame 26. As shown in FIG. 3, the balloon-expandable frame 34 is embodied as a balloon-expandable stent 38 that extends distally from the proximal end 28 of the component 12 and has a length 40 of approximately 15 mm. In other embodiments, the stent 38 may be longer or shorter depending on, for example, the patient's anatomy. The stent 38 is tubular and is constructed of a metallic material, such as, nitinol, stainless steel, or other implant grade metallic material, in an open-cell configuration. It should be appreciated that in other embodiments the stent 38 may be formed from a polymeric material and may be formed in, for example, a Z-stent configuration. In the illustrative embodiment, the outer surface 42 of the stent 38 is covered with low-profile polyester, ePTFE, or other nonporous covering material 44 that prevents fluid from passing through the outer surface 42. However, it should be appreciated that the stent 38 may be covered with standard polyester or other nonporous materials.

As shown in FIG. 3, the stent 38 of the balloon-expandable frame 34 has a diameter 46. As described in greater detail below, the balloon-expandable frame 34 is expandable during implantation from an unexpended diameter (not shown) to the expanded diameter 46. In the illustrative embodiment, the expanded diameter 46 is equal to approximately 26 mm when the frame 34 is expanded. In other embodiments, the expanded diameter may be greater than or less than 26 mm depending on, for example, the patient's anatomy. Examples of balloon-expandable stents are described in U.S. Pat. No. 5,102,417 entitled "Expandable Intraluminal Graft, and Method and Apparatus for Implanting an Expandable Intraluminal Graft" by Julio C. Palmaz and U.S. Pat. No. 6,582,462 entitled "Valve Prosthesis for Implantation in the Body and a Catheter for Implanting Such Valve Prosthesis" by Henning Rud Andersen et al., which are expressly incorporated herein by reference. In the illustrative embodiment, the diameter 46 is oversized relative to the diameter of the aortic annulus 210 (see FIG. 1) such that an interference fit is created between the stent 38 and the annulus 210 when the component 12 is implanted and the stent 38 is expanded, as described in greater detail below.

The balloon-expandable frame 34 is attached to a self-expanding frame 50. In the illustrative embodiment, the distal end 52 of the balloon-expandable frame 34 is secured to the proximal end 54 of the frame 50 by stitching or sewing the frames 34, 50 together, thereby forming the frame 26 of the component 12. It should be appreciated that in other embodiments the frames 34, 50 may be secured together via welding or other fasteners. The frames 34, 50 may also be formed as a single, monolithic frame.

As shown in FIG. 3, the self-expanding frame 50 has a generally hourglass shape and is formed from a metallic material, such as, nitinol, stainless steel, or other implant grade metallic material. It should be appreciated that in other embodiments the frame 50 may be formed from a polymeric material. The frame 50 includes an inwardly tapered proximal section 60, an outwardly tapered middle section 62, and an elongated distal section 64. The section 60 includes the proximal end 54 of the frame 50 and has a distal end 66 connected to the proximal end 68 of the outwardly tapered middle section 62. The section 60 tapers inwardly between the ends 54, 66 from approximately 26 mm at the end 54 to approximately 22 mm at the end 66. In the illustrative embodiment, the proximal section 60 has a length 70 of approximately 10 mm. It should be appreciated that in other embodiments the dimensions of the section 60 may vary depending on, for example, the patient's anatomy.

The outwardly tapered middle section 62 of the self-expanding frame 50 has the proximal end 68 and a distal end 72 connected to the proximal end 74 of the elongated distal section 64. The section 62 tapers outwardly from a diameter of approximately 22 mm at the end 68 to a diameter of approximately 28 mm at the end 72. In the illustrative embodiment, the middle section 62 has a length 76 of approximately 10 mm. In other embodiments, the dimensions of the section 62 may vary depending on, for example, the patient's anatomy. Among other things, the tapered sections 60, 62 of the proximal component 12 permit the placement of the stents 24 that extend from the distal component 14 to the coronary arteries, as described in greater detail below.

The elongated distal section 64 of the self-expanding frame 50 extends distally from the proximal end 74 to the distal end 30 of the component 12. In the illustrative embodiment, the section 64 has a length 78 that is greater than the combined length of the tapered sections 60, 62. In one particular non-limiting example, the length 78 of the elongated distal section 64 is approximately 25 mm and has a diameter 80 of approximately 28 mm. In other embodiments, the dimensions of the section 64 may vary depending on, for example, the patient's anatomy. In one exemplary embodiment, the distal section 64 may taper between the proximal end 74 and the distal end 30.

As shown in FIG. 3, the proximal section 60 of the self-expanding frame 50 is formed in an open-cell stent configuration, and the sections 62, 64 are formed in a Z-stent configuration. It should be appreciated that in other embodiments the sections 60, 62, 64 may be formed in a single configuration, including an open-cell stent configuration or Z-stent configuration. The sections 60, 62, 64 may also be formed as a single monolithic component. The outer surface 82 of the self-expanding frame 50 is covered with low profile polyester, ePTFE, or other nonporous covering material 84 such that fluid is prevented from passing through the surface 82. In that way, the entire outer surface of the component 12 is covered to prevent fluid from passing therethrough. The covering material 84 immediately distal to the balloon-expandable frame 34 is equipped with a "trap door" 86, which may be opened to permit the passage of one or more surgical instruments for embolization of possible paravalvular leaks. The entire outer surface of component 12 may be also covered with low-profile Dacron or other synthetic material. It should also be appreciated that all or part of the component 12 may be covered with hydrogel or other sealing material.

As described above, the device 10 also includes a distal component 14, which is secured to the distal end 30 of the proximal component 12 when the device 10 is implanted in the patient's aorta 16. Referring now to FIG. 4, the distal component 14 includes a frame 100 that extends from a proximal end 102 configured to be secured to the proximal component 12 to a distal end 104. The frame 100 has a passageway 106 defined therein, which extends through the ends 102, 104 of the component 14. The passageway 106 has a diameter 108 and is sized to receive the distal end 30 of the proximal component 12 when the device 10 is assembled.

In the illustrative embodiment, the components 12, 14 are secured together via an interference fit between the frame 100 and the distal end 30 of the proximal component 12. Specifically, the diameter 108 of the passageway 106 is less than the diameter 80 of the proximal component 12. In the illustrative embodiment, the diameter 108 is equal to approximately 26 mm. It should be appreciated that in other embodiments the components 12, 14 may be secured together via stitching or other fastening means.

As shown in FIG. 4, the component 14 includes a proximal frame 110 that is connected to an elongated distal frame 112. The proximal frame 110 and the distal frame 112 are formed from metallic materials, such as, nitinol, stainless steel, or other implant grade metallic materials. It should be appreciated that in other embodiments the frames 110, 112 may be formed from a polymeric material. The proximal frame 110 is formed in a Z-stent configuration, and the distal frame 112 is formed in an open-cell configuration. Each of the frames 110, 112 is self-expanding. In the illustrative embodiment, the distal frame 112 is secured to the distal end 114 of the proximal frame 110 by stitching or sewing the frames 110, 112 together. It should be appreciated that in other embodiments the frames 110, 112 may be secured together via welding or other fasteners. The frames 110, 112 may also be formed as a single, monolithic frame.

The proximal frame 110 has an outer surface 120 that is covered with low profile polyester, ePTFE, or other nonporous covering material 122. As a result, fluid is prevented from passing through the surface 120. The distal frame 112 is uncovered such that fluid is permitted to pass through the openings 124 formed therein.

As shown in FIG. 4, the proximal frame 110 includes a proximal section 126, an outwardly tapered section 128 extending distally from the proximal section 126, and an elongated distal section 130. The proximal section 126 includes the proximal end 102 of the component 14 and has a distal end 132 connected to the proximal end 134 of the outwardly tapered section 128. In the illustrative embodiment, the proximal section 126 has a length 136 of approximately 25 mm. It should be appreciated that in other embodiments the dimensions of the section 126 may vary depending on, for example, the patient's anatomy.

The tapered section 128 of the frame 110 has the proximal end 134 and a distal end 140 connected to the proximal end 142 of the elongated distal section 130. The section 128 tapers outwardly from a diameter of approximately 26 mm at the end 132 to a diameter between approximately 44 mm and 48 mm at the end 140. In the illustrative embodiment, the tapered section 128 has a length 146 of approximately 10 mm. It should be appreciated that in other embodiments the dimensions of the section 128 may vary depending on, for example, the patient's anatomy.

The elongated distal section 130 of the frame 110 extends distally from the proximal end 142 to the distal end 114 of the frame 110. In the illustrative embodiment, the section 130 has a length 150. In one particular non-limiting example, the length 150 of the elongated distal section 130 is approximately 20 mm. The section 130 also has a diameter 152 of between approximately 44 mm and 48 mm. In other embodiments, the dimensions of the section 130 may vary depending on, for example, the patient's anatomy.

As described above, the distal component 14 also includes a pair of conduits 22, which are connected to the proximal frame 110. Each conduit 22 has a distal end 160 secured to the tapered section 128 of the frame 110 and a proximal end 162 positioned adjacent to the proximal end 102 of the component 12. As shown in FIG. 4, the conduit 22 does not extend beyond the proximal end 102 of the component 12. Each conduit 22 has a passageway 164 that extends through the ends 160, 162 and is sized to receive a stent 24.

The passageway 164 has a proximal opening 166 defined in the end 162. The opening 166 has a diameter 168 that in the exemplary embodiment is equal to approximately 5 mm. As shown in FIG. 5, the passageway 164 has a distal opening 170 that is defined in the end 160 and the tapered section 128 of the frame 110. The distal opening 170 has a diameter 172 that is greater than the diameter 168. In the illustrative embodiment, the diameter 172 is equal to approximately 8 mm. The passageway 164 measures approximately 8 mm in diameter over a distance 174 of approximately 5 mm and tapers smoothly into the approximately 5 mm diameter 168 at a junction 176. The passageway 164 maintains the diameter 168 between the junction 176 and the proximal opening 166. In the illustrative embodiment, the passageway 164 has a length 180 of approximately 2 cm between the junction 176 and the proximal opening 166.

Each conduit 22 is wire reinforced and allows for passage of catheters or stents 24 and easier cannulation of the coronary ostia, regardless of deployment orientation. This configuration allows stenting of the coronary arteries 182 (see FIG. 1) prior to the deployment of component 12, as described in greater detail below. In the illustrative embodiment, the tapered section 128 permits the uncompromised passage of stents 24 into the coronary arteries 182 in such a way that the stents are not compressed between the sinutubular junction and the device 10 itself.

As shown in FIG. 4, the elongated distal frame 112 of the component 14 extends distally from the distal end 114 of the frame 110 to the distal end 104 of the component 14. In the illustrative embodiment, the frame 112 has a length 190. In one particular non-limiting example, the length 190 of the elongated frame 112 is approximately 10 cm, which is sufficient to cover the arch 20 of the aorta 18 when implanted therein. In other embodiments, the dimensions of the frame 112 may vary depending on, for example, the patient's anatomy. The distal frame 112 permits the accurate deployment of component 14 without compromising the circulation to supra-aortic branches. It also allows for cannulation of the supra-aortic branches, if placement of a fenestrated/branch arch device is necessary.

Figure 6:
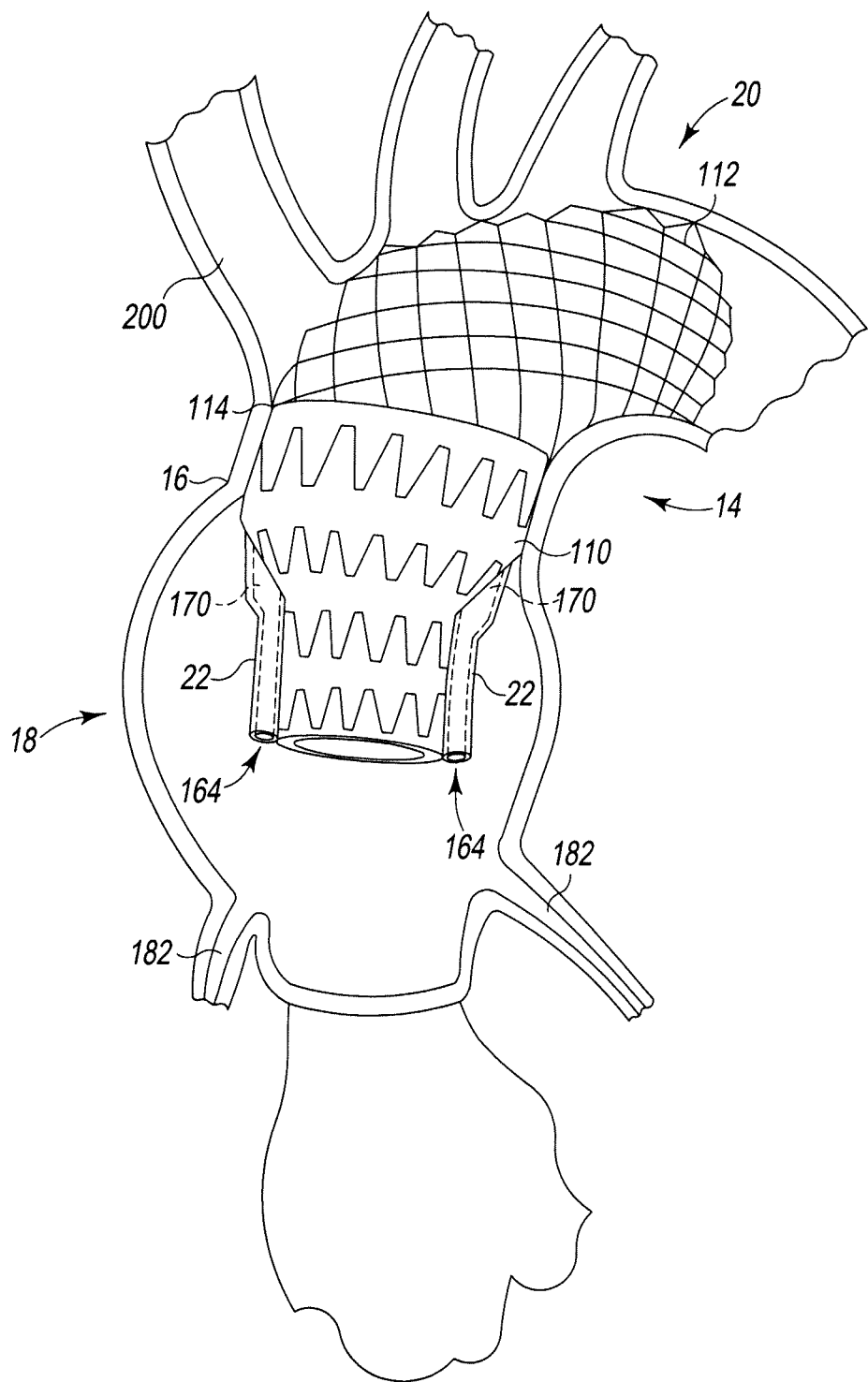
FIG. 6 is a partial cutaway view of the aorta with the distal prosthetic component of FIG. 3 implanted therein.

To implant the device 10 in the patient's aorta 16, a surgeon may obtain open exposure or percutaneous access to the common femoral artery. The iliac arteries or an iliac conduit may also be used. After obtaining access and placing a stiff wire in the ascending aorta 18, the device 10 and the delivery system are prepared. In the illustrative embodiment, the delivery system is composed of a 100-105 cm hydrophilic sheath. As shown in FIG. 6, the distal component 14 is delivered first. After performing a lateral oblique thoracic aortogram, the component 14 is deployed such that the distal end 114 of the proximal frame 110 is positioned proximal to the innominate artery 200, thereby ensuring that the distal openings 170 of the conduits 22 are at 12 and 6 o'clock positions in relationship to the innominate artery 200.

Figure 7:
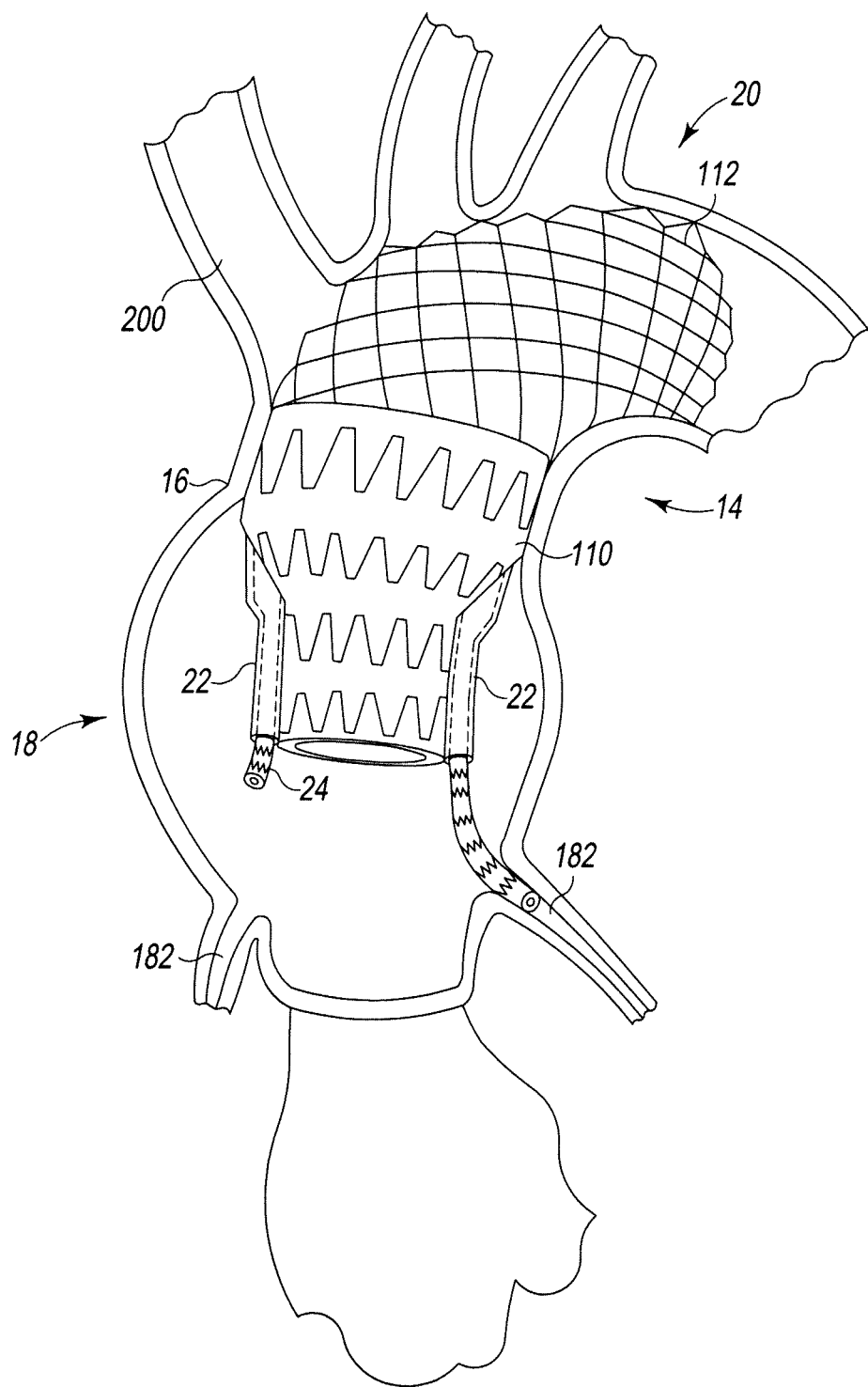
FIG. 7 is a view similar to FIG. 6 showing stents extending from the distal prosthetic component.

Using the contralateral common femoral artery wires, standard coronary guide catheters are introduced through the distal frame 112 of the component 14 into each conduit 22. The conduits 22 may then be cannulated with the catheters prior to insertion of the stents 24. Alternatively, the conduits 22 may be pre-cannulated. Using the catheters, access is obtained to the right and left coronary arteries 182. The stents 24 are advanced into the passageways 164 through the distal openings 170 and out of the conduits 22 to bridge the arteries 182 and the conduits 22, as shown in FIG. 7. In that way, each artery 182 is connected to its respective conduit 22. Each stent 24 is covered and may be embodied as a balloon-expandable stent or a self-expanding stent. It should be appreciated that coronary artery bypasses may be performed to the right and left coronary systems prior to the placement of the component 14.

The proximal component 12 may be deployed after the implantation of the distal component 14. The components 12, 14 may be deployed in a single surgical procedure taking place on a single day or the component 14 may be deployed in one procedure, and the component 12 may be deployed in another, separate procedure at a later date. As shown in FIG. 1, the proximal component 12 is deployed into the position across the native aortic valve 202.

To do so, a stiff wire is passed through the aortic valve 202 into the left ventricle 204. The delivery system for the proximal component 12 is passed through the valve 202. An example of a delivery system is described in U.S. Pat. No. 5,102,417 entitled "Expandable Intraluminal Graft, and Method and Apparatus for Implanting an Expandable Intraluminal Graft" by Julio C. Palmaz, which is incorporated herein by reference. When the delivery system is in position, the proximal component 12 is released by unsheathing the system, thereby permitting expansion of the self-expanding frame 50. As described above, the self-expanding frame 50 engages the proximal end 102 of the distal component 14 to secure the components 12, 14 together and seal the distal end 30 of the component 12 within the distal component 14. As shown in FIG. 2, the proximal end 28 of the proximal component 12 is positioned in the aortic annulus, and the hour-glass shape of the component 12 provides a space for the native aortic valve leaflets such that the leaflets are not pressed against or over the openings of coronary arteries 182.

The balloon-expandable frame 34 may be now deployed by inflating the balloon within the delivery system. This deploys the frame 34 to the predetermined expanded diameter 46 and advances the frame 34 into engagement with the aortic annulus 210, thereby sealing the aortic annulus 210 such that fluid is permitted to pass from the left ventricle 204 only through the valve 32. As shown FIG. 1, the valve 32 is positioned in the aortic annulus 210 proximal to the coronary arteries 182. It should be appreciated that the deployment of the component 12 may be performed during rapid ventricular pacing (RVP). In cases with aortic stenosis, the valve 32 may be dilated with balloon angioplasty prior to the introduction of the proximal component 12.

Referring now to FIGS. 8-16, another embodiment of a proximal component 212 of the device 10 is shown. Some features of the embodiment illustrated in FIGS. 8-16 are substantially similar to those described above in reference to the embodiment of FIGS. 1-7. Such features are designated in FIGS. 8-16 with the same reference numbers as those used in FIGS. 1-7. Similar to the proximal component 12 of FIGS. 1-7, the proximal component 212 may be secured to the distal component 14 when implanted into a patient's aorta 16. When implanted, the proximal component 212 is positioned in the patient's ascending aorta 18, while the distal component 14 extends distally into the arch 20 of the patient's aorta 16.

Figure 8:
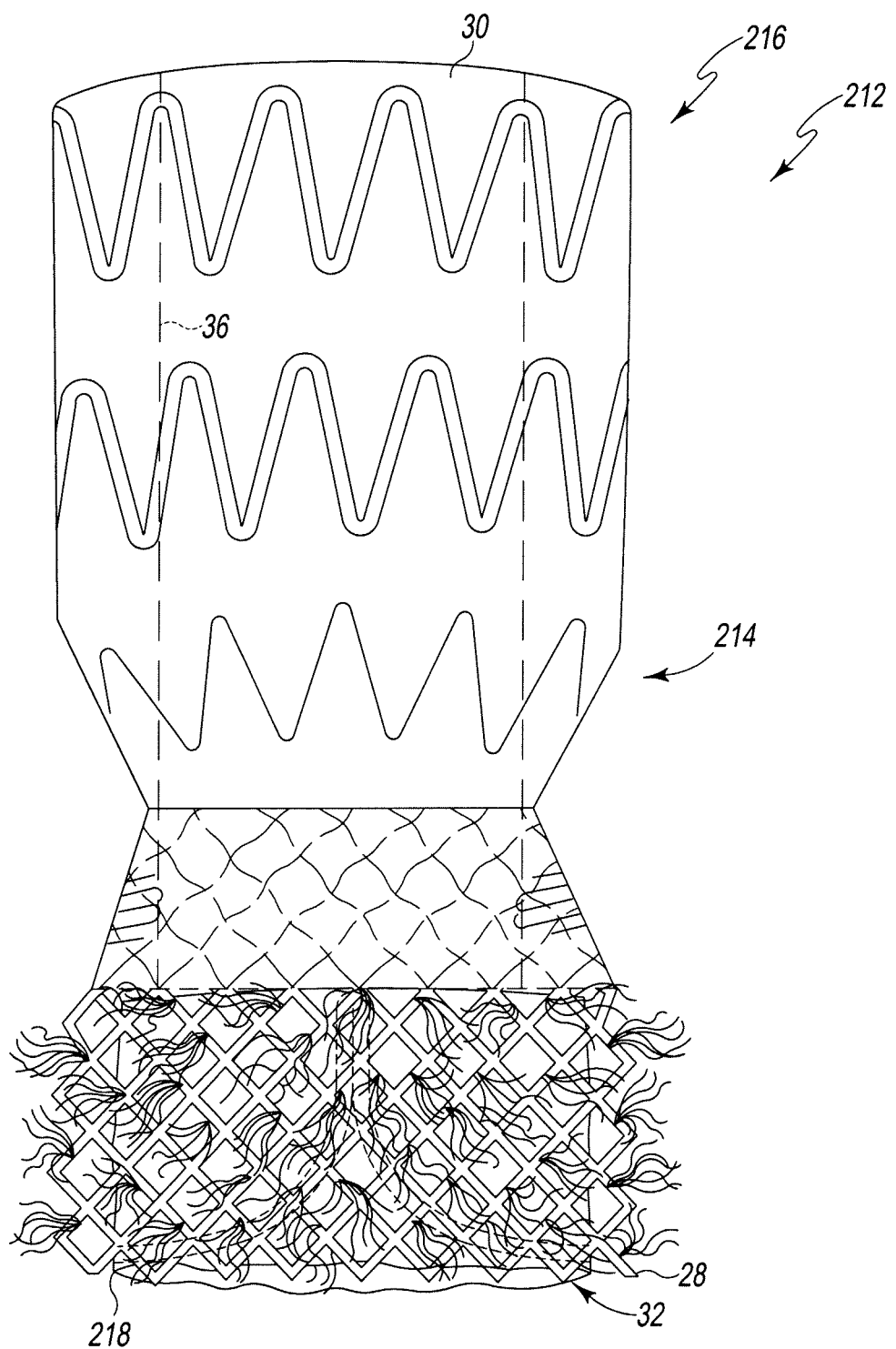
FIG. 8 is an elevation view of another embodiment of a proximal prosthetic component of the endovascular prosthetic device of FIG. 2.

As shown in FIG. 8, the proximal component 212 includes a dual-frame 214 that extends from a proximal end 28 to a distal end 30. The frame 214 is attached to a valve 32 (shown in phantom), which is positioned at the proximal end 28 of the component 212. In the illustrative embodiment, the valve 32 is configured as a bicuspid valve. It should be appreciated that in other embodiments the valve 32 may be tricuspid or quadracuspid. The valve 32 may be constructed from treated bovine pericardium or other suitable proven biological or synthetic material. When the proximal component 212 is implanted into the patient's aorta 16, the valve 32 replaces the aortic valve and permits fluid (i.e., blood) to selectively pass from the heart and into a passageway 36 extending through the proximal component 212.

Figure 9:
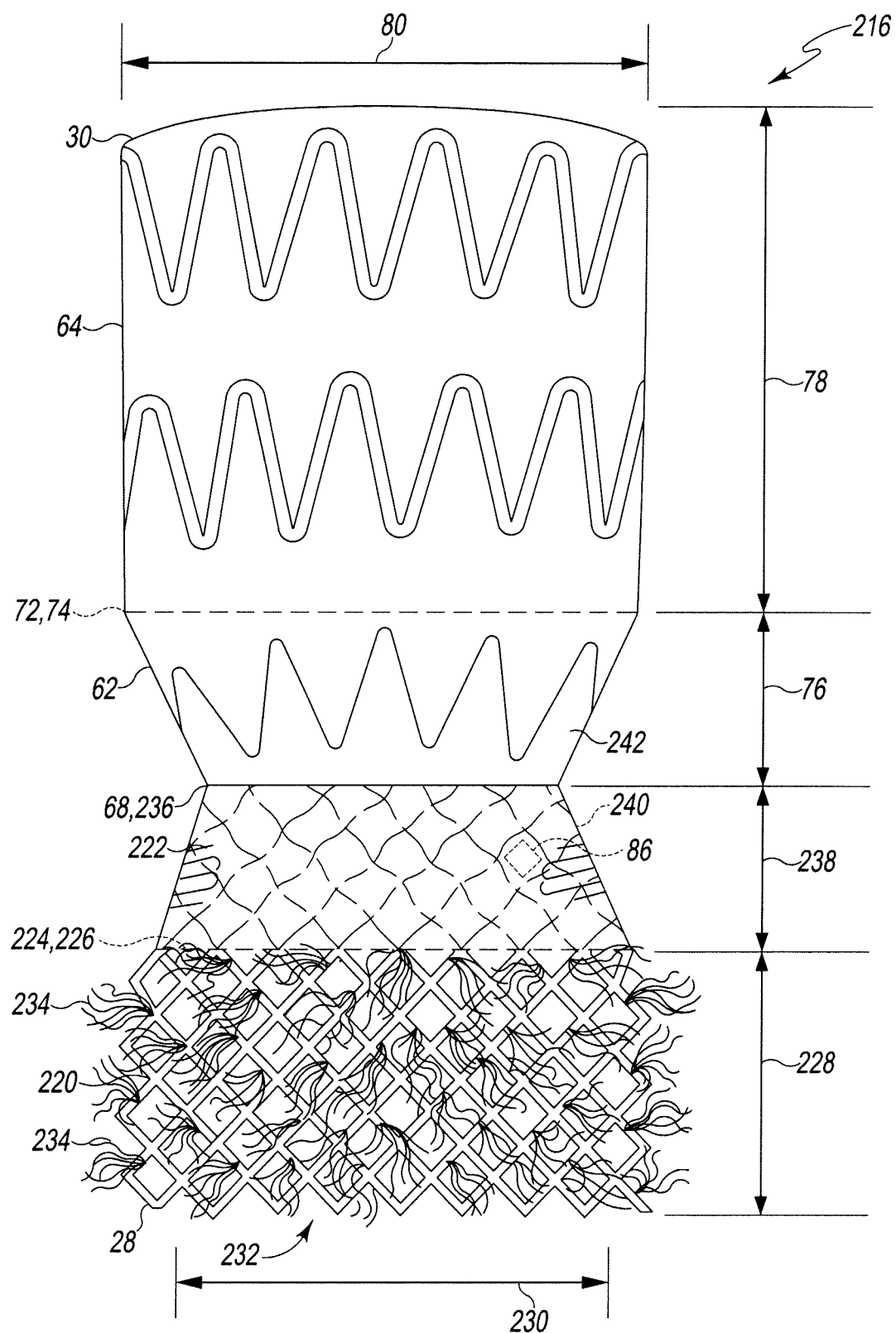
FIG. 9 is an elevation view of a self-expanding outer frame of the proximal prosthetic component of FIG. 8.

The dual-frame 214 of the proximal component 212 includes a self-expanding outer frame 216 and a balloon-expandable inner frame 218 that is secured to the self-expanding outer frame 216 and houses the valve 32. Referring now to FIG. 9, the self-expanding outer frame 216 has a generally hourglass shape and is formed from a metallic material, such as, nitinol, stainless steel, or other implant grade metallic material. It should be appreciated that in other embodiments the outer frame 216 may be formed from a polymeric material. The outer frame 216 includes an elongated proximal section 220, an inwardly tapered section 222, an outwardly tapered middle section 62, and an elongated distal section 64.

The elongated proximal section 220 of the outer frame 216 includes the proximal end 28 of the component 212 and has a distal end 224 connected to a proximal end 226 of the inwardly tapered section 222. The proximal section 220 is embodied as a tubular stent. It should be appreciated that in other embodiments the section 220 may be shaped as a prism, cone, or other geometric shape depending on the patient's anatomy.

In the illustrative embodiment, the proximal section 220 has a length 228 that is equal to approximately 15 mm. The proximal section 220 also has a diameter 230 of approximately 32 mm. It should be appreciated that in other embodiments the dimensions of the frame 216 may vary according to the anatomy of the patient. In the illustrative embodiment, the diameter 230 is oversized relative to the diameter of the aortic annulus 210 such that an interference fit is created between the proximal section 220 and the annulus 210 when the component 212 is implanted, as described in greater detail below. As shown in FIG. 9, the proximal section 220 defines a passageway 232 in the outer frame 216.

In the illustrative embodiment, collagen fibers 234 are attached to the proximal section 220 to aid in preventing paravalvular leaks and migration of the proximal component 212 within the aortic walls. The fibers 234 extend outwardly from the proximal section 220 and inwardly into the passageway 232. It should be appreciated that in other embodiments the outer frame 216 may be covered with hydrogel or other sealing materials. In other embodiments, a plurality of barbs or hooks may be attached to the proximal section 220. The hooks may be configured to further engage the tissue of the aorta and inhibit or prevent migration of the device 10.

The inwardly tapered section 222 of the outer frame 216 includes the proximal end 226 and has a distal end 236 connected to the proximal end 68 of the outwardly tapered middle section 62. The section 222 tapers inwardly between the ends 226, 236 from approximately 32 mm at the end 226 to approximately 22 mm at the end 236. In the illustrative embodiment, the inwardly tapered section 222 has a length 238 of approximately 10 mm.

The outwardly tapered middle section 62 of the self-expanding frame 216 has the proximal end 68 and a distal end 72 connected to the proximal end 74 of the elongated distal section 64. The section 62 tapers outwardly from a diameter of approximately 22 mm at the end 68 to a diameter of approximately 28 mm at the end 72. In the illustrative embodiment, the middle section 62 has a length 76 of approximately 10 mm. In other embodiments, the dimensions of the section 62 may vary depending on, for example, the patient's anatomy.

The elongated distal section 64 of the self-expanding frame 216 extends distally from the proximal end 74 to the distal end 30 of the component 212. In the illustrative embodiment, the section 64 has a length 78 that is greater than the combined length of the tapered sections 60, 62. In one particular non-limiting example, the length 78 of the elongated distal section 64 is approximately 30 mm and has a diameter 80 of approximately 34 mm. In other embodiments, the dimensions of the section 64 may vary depending on, for example, the patient's anatomy. In one exemplary embodiment, the distal section 64 may taper between the proximal end 74 and the distal end 30.

As shown in FIG. 9, the proximal section 220 and the inwardly tapered section 222 of the self-expanding frame 216 are formed in an open-cell stent configuration, and the sections 62, 64 are formed in a Z-stent configuration. It should be appreciated that in other embodiments the sections 62, 64, 220, 222 may be formed in a single configuration, including an open-cell stent configuration or Z-stent configuration. The sections 62, 64, 220, 222 may also be formed as a single monolithic component. The outer surface 240 of the sections 62, 64, 222 are covered with low profile polyester, ePTFE, or other nonporous covering material 242 such that fluid is prevented from passing through the surface 240. The covering material 242 immediately distal to the proximal section 220 is equipped with a "trap door" 86, which may be opened to permit the passage of one or more surgical instruments for embolization of possible paravalvular leaks. The outer surface 240 of the sections 62, 64, 222 may be also covered with low-profile Dacron or other synthetic material. It should also be appreciated that all or part of the frame 216 may be covered with hydrogel or other sealing material.

Figure 10:
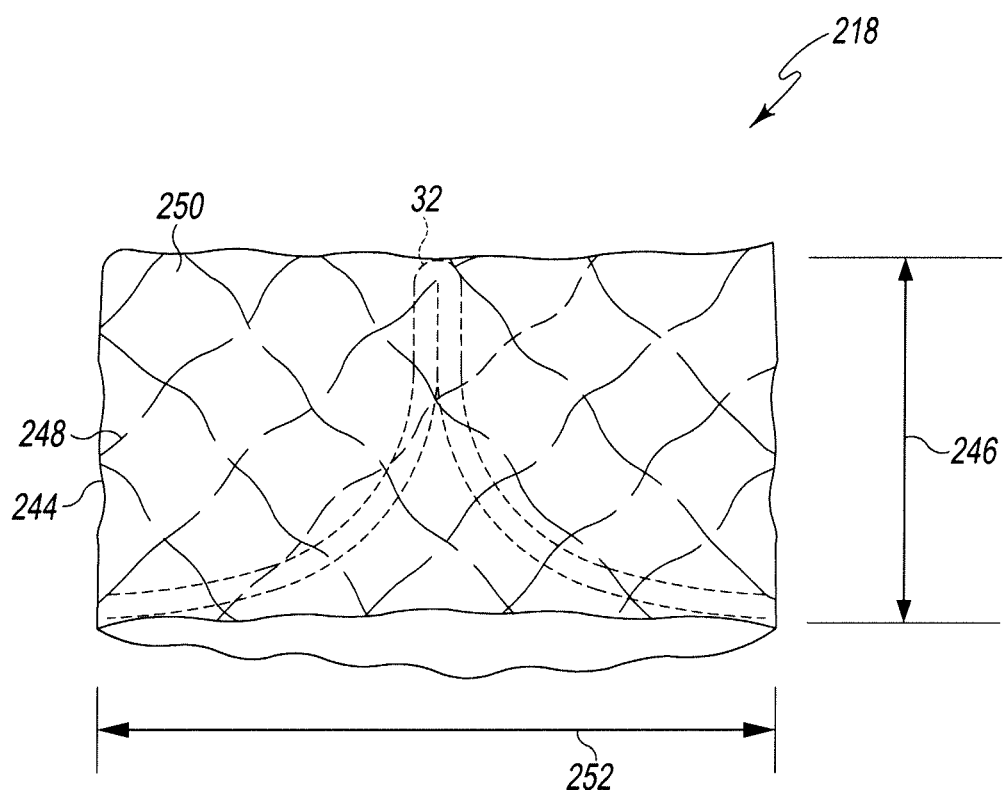
FIG. 10 is an elevation view of a balloon-expandable inner frame of the proximal prosthetic component of FIG. 8.

As described above, the outer frame 216 of the dual-frame 214 is secured to a balloon-expandable inner frame 218, which is positioned in the passageway 232. As shown in FIG. 10, the frame 218 houses the valve 32. The balloon-expandable frame 218 is embodied as a balloon-expandable tubular stent 244 that has a length 246 of approximately 15 mm. In other embodiments, the stent 244 may be longer or shorter depending on, for example, the patient's anatomy. The stent 244 is tubular and is constructed of a metallic material, such as, nitinol, stainless steel, or other implant grade metallic material, in an open-cell configuration. It should be appreciated that in other embodiments the stent 244 may be formed from a polymeric material and may be formed in, for example, a Z-stent configuration. In the illustrative embodiment, the outer surface 248 of the stent 244 is covered with low-profile polyester, ePTFE, or other nonporous covering material 250 that prevents fluid from passing through the outer surface 248. However, it should be appreciated that the stent 244 may be covered with standard polyester, ePTFE or other nonporous materials.

As shown in FIG. 10, the stent 244 of the inner frame 218 has a diameter 252. As described in greater detail below, the balloon-expandable frame 218 is expandable during implantation from an unexpanded diameter (not shown) to the expanded diameter 252. In the illustrative embodiment, the expanded diameter 252 is equal to approximately 26 mm when the inner frame 218 is expanded. In other embodiments, the expanded diameter may be equal to, or greater than, the diameter 230 of the proximal section 220 of the outer frame 216. In the illustrative embodiment, the expanded diameter 252 is oversized relative to the diameter of the aortic annulus 210 such that an interference fit is created between the proximal section 220 and the annulus 210 when the component 212 is implanted, and the inner frame 218 is expanded, as described in greater detail below.

Figure 11:
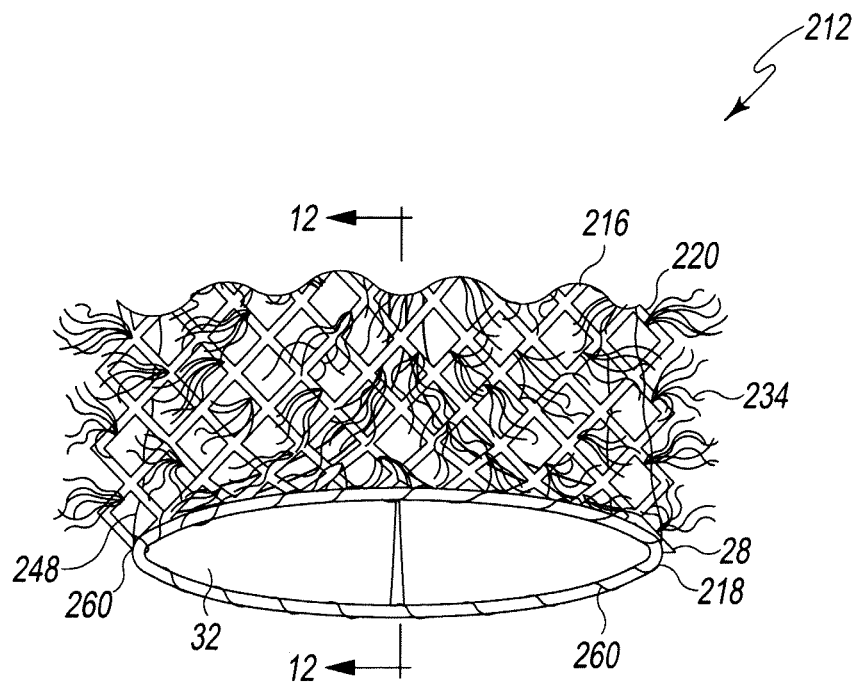
FIG. 11 is a perspective view a proximal end of the proximal prosthetic component of FIG. 8.
Figure 12:
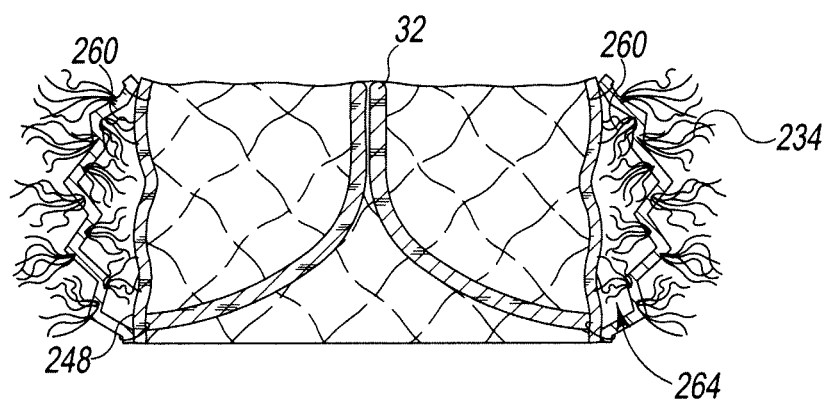
FIG. 12 is a cross-sectional elevation view of the proximal prosthetic component of FIG. 8 taken along the line 12-12 in FIG. 11.
Figure 13:
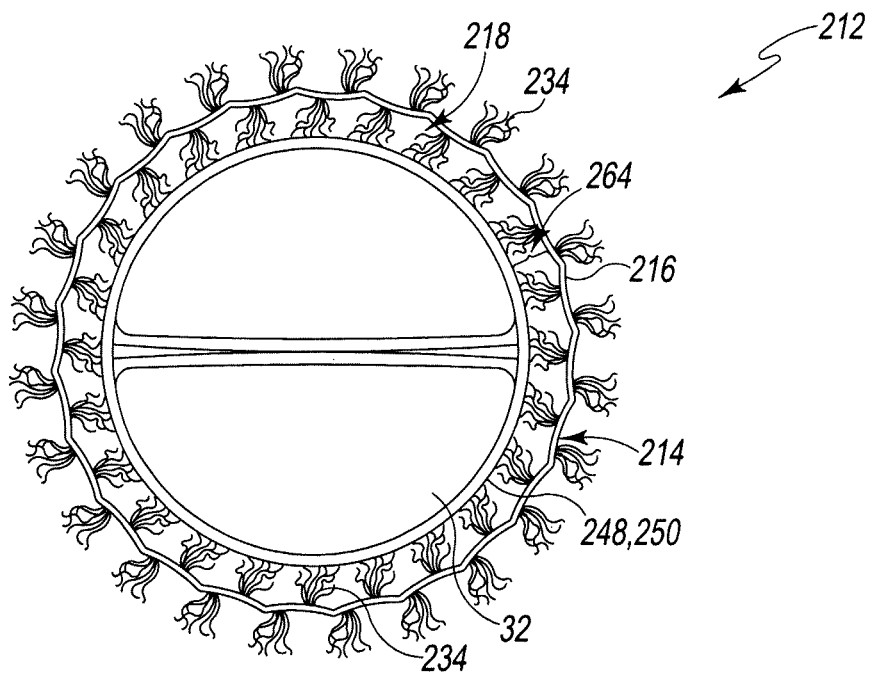
FIG. 13 is a plan view of the proximal prosthetic component of FIG. 8 showing the inner frame in an unexpanded position.

Referring now to FIG. 11, the inner frame 218 of the dual-frame component 214 is secured to the outer frame 216 via a plurality of stitches 260. It should be appreciated that in other embodiments soldering, welding or other fasteners may be used to secure the inner frame 218 to the outer frame 216. As shown in FIGS. 11-14, the inner frame 218 and the valve component 32 are positioned in the passageway 232 defined in the self-expanding frame 216. When the inner frame 218 is unexpanded, the outer surface 248 of the stent 244 is spaced apart from the fibers 234 attached to the outer frame 216. In the illustrative embodiment, a gap 264 is defined therebetween, and the gap 264 has a magnitude of about 2 mm to about 3 mm.

Figure 14:
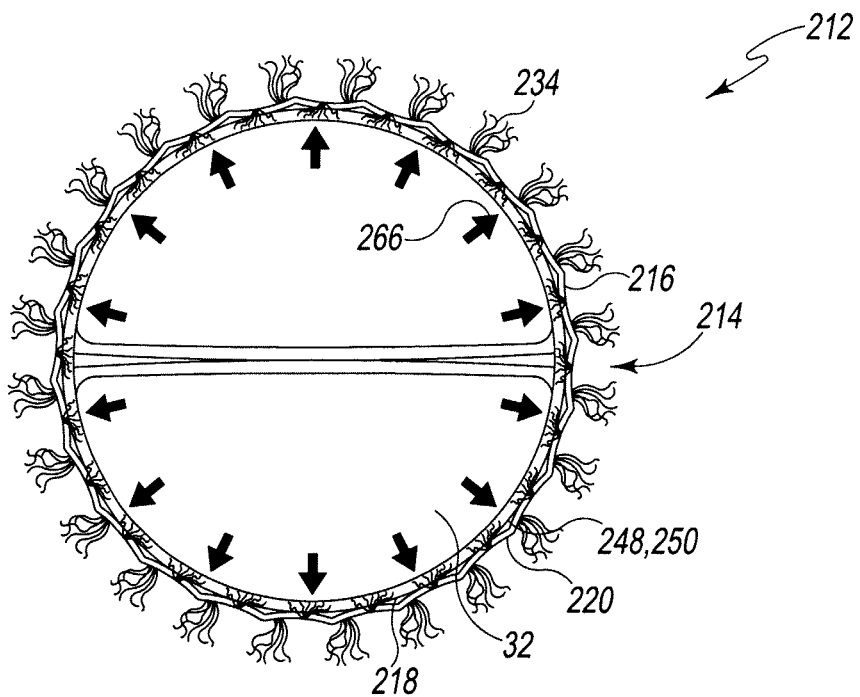
FIG. 14 is a plan view similar to FIG. 13 showing the inner frame in an expanded position.

As shown in FIG. 14, the balloon-expandable inner frame 218 may be expanded in the direction indicated by arrows 266. As described above, the diameter 230 of the proximal section 220 of the outer frame 216 is oversized relative to the diameter of the aortic annulus 210. As such, when the component 212 is implanted, the proximal section 220 is reduced to the diameter of the annulus 210. Because the expanded diameter 252 of the stent 244 is greater than the diameter of the annulus, the outer surface 248 of the stent 244 engages the fibers 234 (and hence the inner surface of the proximal section 220 of the outer frame 216) through the covering material 250. In that way, the gap 264 is closed, and the fibers 234 and the covering material 250 create a seal between the inner frame 218 and the outer frame 216.

To implant an endograft device 10 that includes proximal component 212 in the patient's aorta 16, a surgeon may obtain open exposure or percutaneous access to the common femoral artery. The surgeon may then implant the distal component 14 in the manner described above in regard to FIGS. 1-7 and advance the stents 24 into position in the arteries 182. The proximal component 212 may be deployed after the implantation of the distal component 14. To do so, a stiff wire is passed through the aortic valve 202 into the left ventricle 204. The delivery system for the proximal component 212 is then passed through the valve 202.

When the delivery system is in position, the proximal component 212 is released by unsheathing the system, thereby permitting expansion of the self-expanding frame 216. The self-expanding frame 216 engages the proximal end 102 of the distal component 14 to secure the components 212, 14 together and seal the distal end 30 of the component 212 within the distal component 14.

Figure 15:
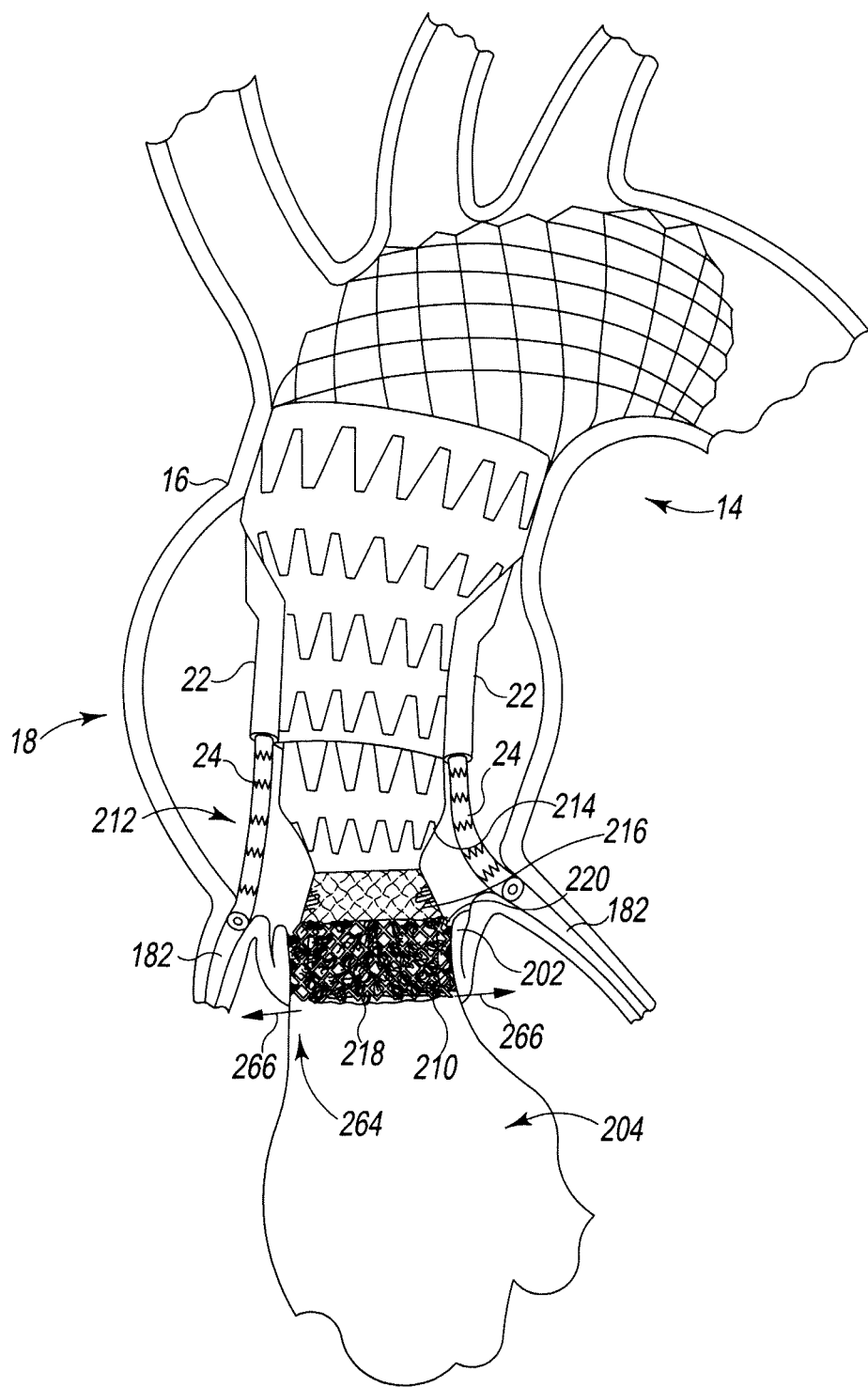
FIG. 15 is a partial cutaway view of the aorta with the distal prosthetic component of FIG. 4 secured to the proximal prosthetic component of FIG. 8.
Figure 16:
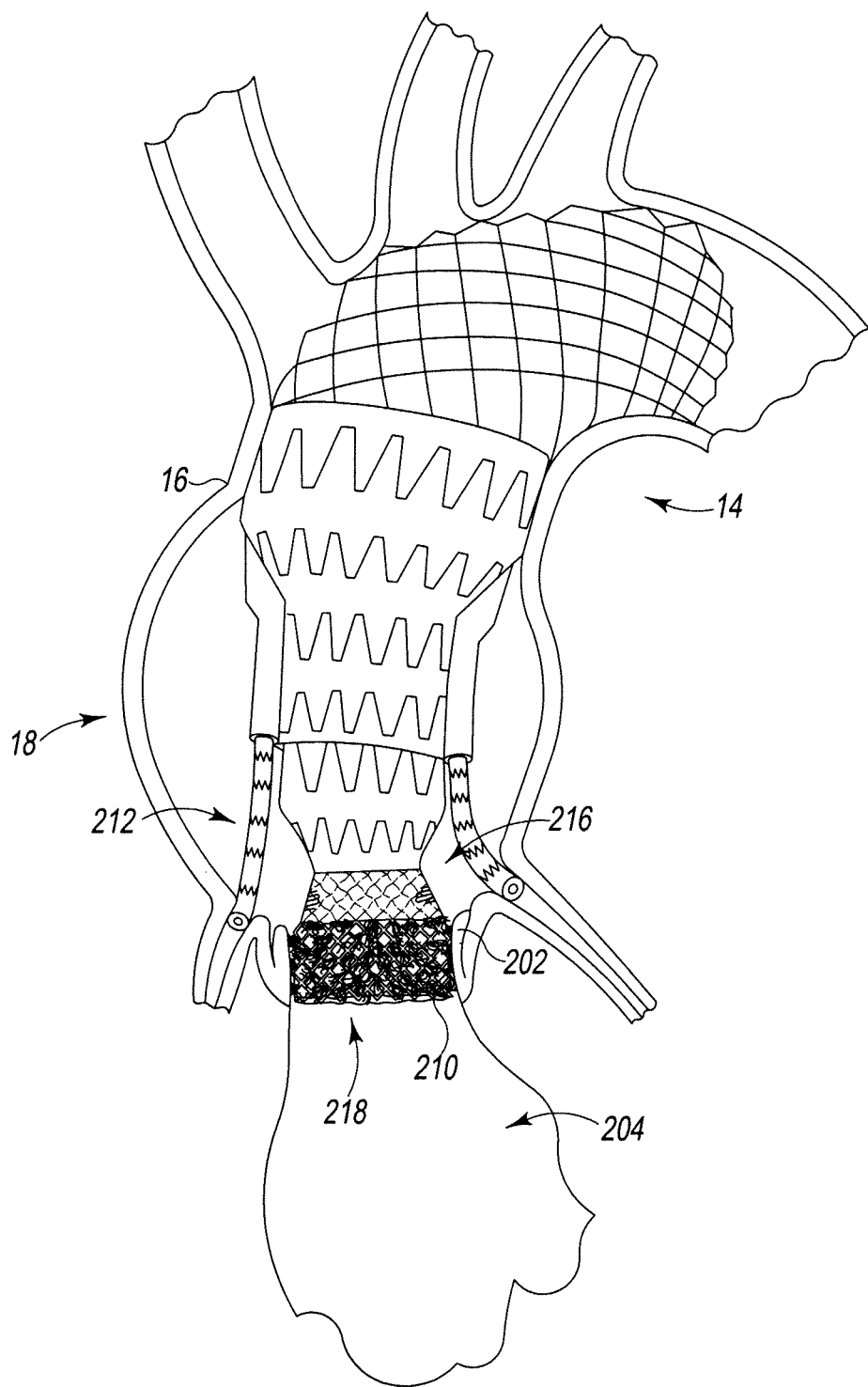
FIG. 16 is a view similar to FIG. 15 showing the inner frame in an expanded position.

When the frame 216 is unsheathed, the proximal section 220 expands into engagement with the aortic annulus 210, thereby creating an interference fit between the frame 216 and the annulus 210 and stabilizing the device 10 in place. As shown in FIG. 15, the inner frame 218 is initially unexpanded within the outer frame 216. The inner frame 218 may be deployed by expanding the balloon assembly. Expansion of the balloon-expandable inner frame 218 engages the inner frame 218 with the outer frame 216 and compresses the collagen fiber/hydrogel coated proximal section 220 of the outer frame 216 against the aortic annulus 210. As shown in FIG. 16, the combined engagement of the frames 216, 218 seals the annulus 210 and the paravalvular areas, and thus, prevents paravalvular leakage. As such, fluid is permitted to pass from the left ventricle 204 only through the valve 32 of the component 212. As shown FIGS. 15-16, the valve 32 is positioned in the aortic annulus 210 proximal to the coronary arteries 182. It should be appreciated that the deployment of the component 212 may be performed during rapid ventricular pacing (RVP). In cases with aortic stenosis, the valve 32 may be dilated with balloon angioplasty prior to the introduction of the proximal component 212.

In each of the embodiments described above, the self-expanding frame portion of proximal components 12, 212 significantly improves the accuracy and control of the deployment of the device 10. The bicuspid configuration of the valve 32 serves three distinct purposes, including (1) by reducing the number of valve commissures to two, the profile will be reduced, (2) the valve 32 may conform better to the aortic annulus, and (3) when the annulus is asymmetrical, the incidence of aortic insufficiency may be reduced.

Referring now to FIGS. 17-22, the proximal component 12 or the proximal component 212 may be used as a transcatheter valve with slight modification. Such a valve may be deployed via a transfemoral or trans-axillary route, as will be described in further detail below.

Figure 17:
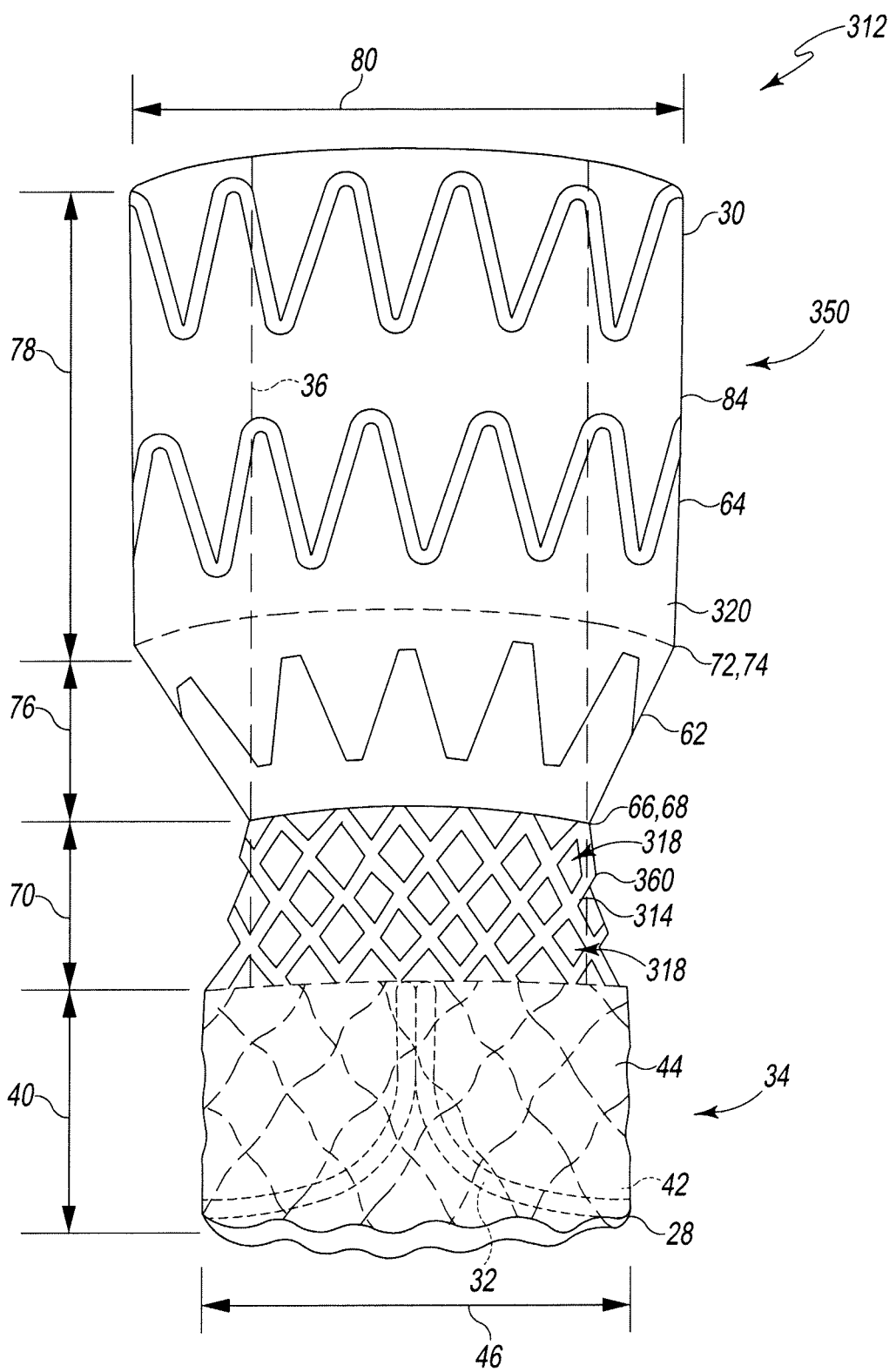
FIG. 17 is an embodiment of a transcatheter valve device similar to the proximal prosthetic component of FIG. 3.
Figure 18:
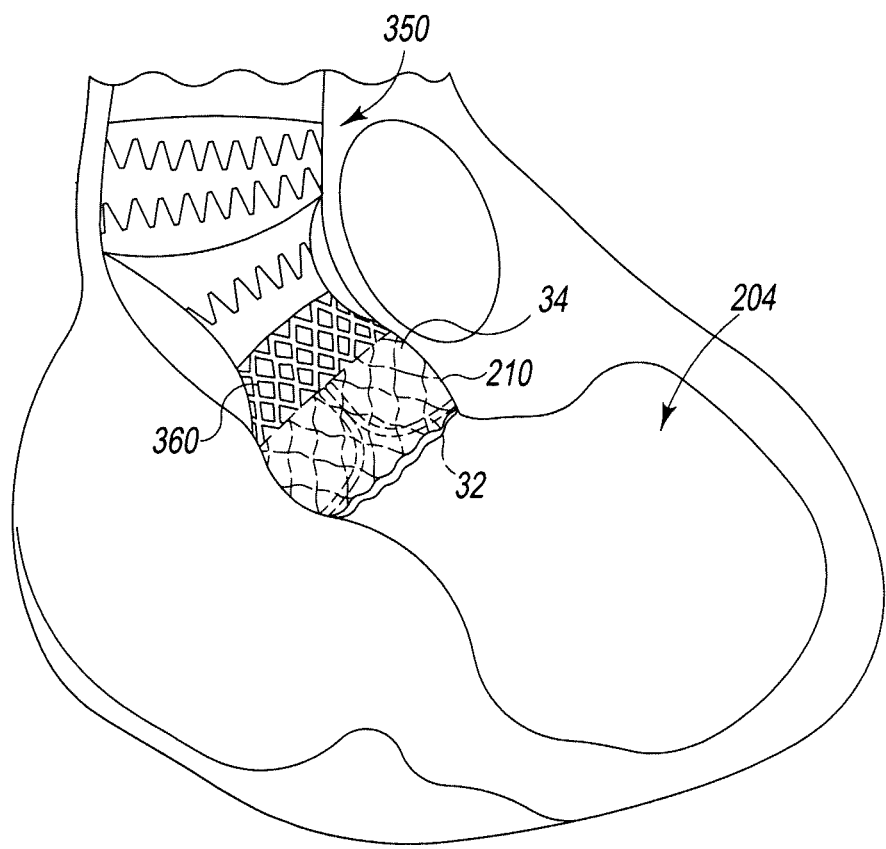
FIGS. 18-19 are partial cutaway views of the aorta with the transcatheter valve of FIG. 17 implanted therein.
Figure 19:
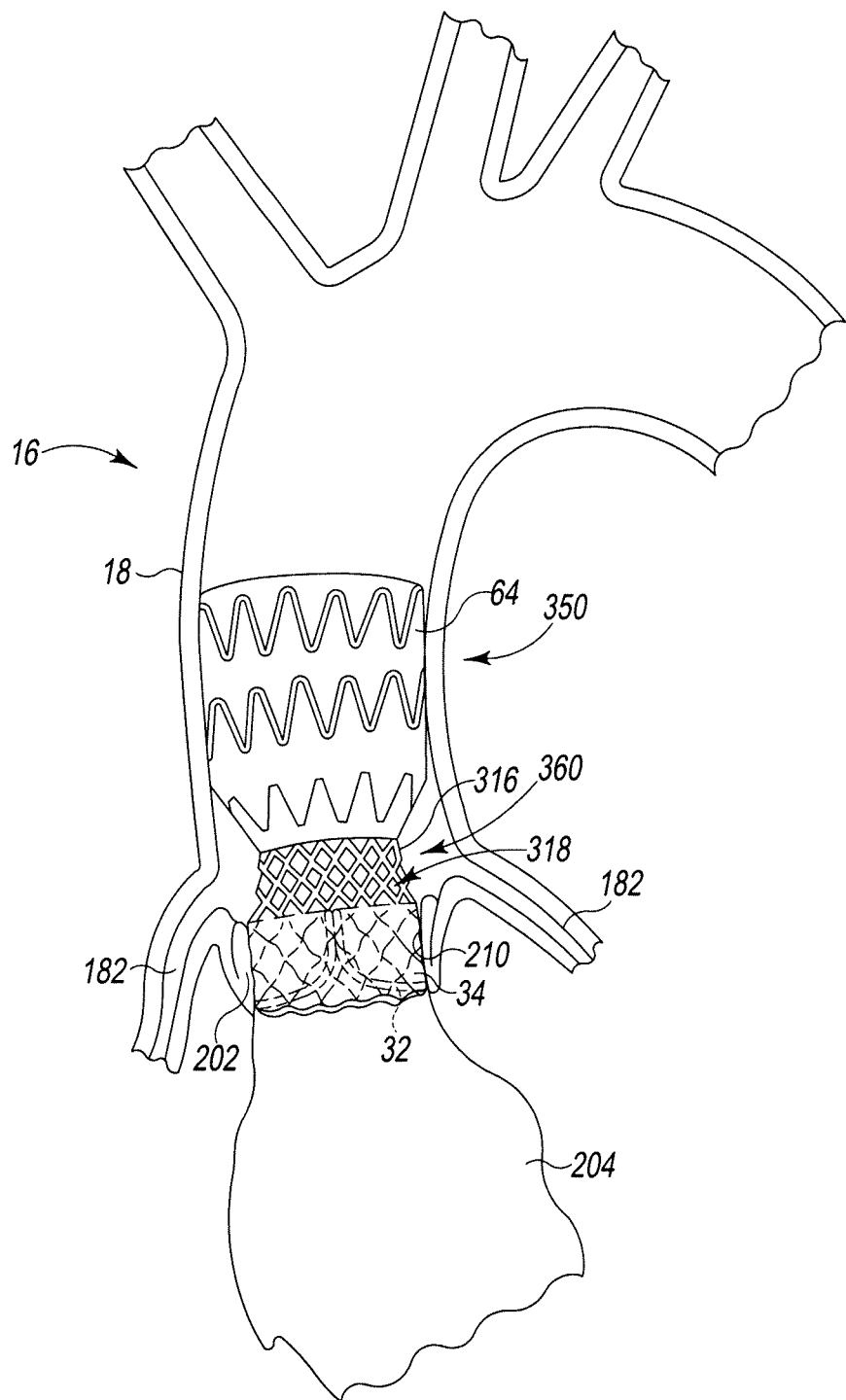

Referring now to FIGS. 17-19, one embodiment of a transcatheter valve component 312 is shown. Some features of the embodiment illustrated in FIGS. 17-19 are substantially similar to those described above in reference to the proximal component 12 of FIGS. 1-7. Such features are designated in FIGS. 17-19 with the same reference numbers as those used in FIGS. 1-7. Similar to the proximal component 12 of FIGS. 1-7, the transcatheter valve component 312 includes a frame 26 that extends from a proximal end 28 to a distal end 30. The frame 326 is attached to a valve 32 (shown in phantom), which is positioned at the proximal end 28 of the valve component 312. When the valve component 312 is implanted into the patient's aorta 16, the valve 32 replaces the aortic valve and permits fluid (i.e., blood) to selectively pass from the heart and into a passageway 36 extending through the valve component 312.

The valve 32 is housed in a balloon-expandable frame 34 of the frame 26. As shown in FIG. 17, the balloon-expandable frame 34 is embodied as a balloon-expandable stent 38 that extends distally from the proximal end 28 of the transcatheter valve component 312 and has a length 40 of approximately 15 mm. In other embodiments, the stent 38 may be longer or shorter depending on, for example, the patient's anatomy. The stent 38 is tubular and is constructed of a metallic material, such as, nitinol, stainless steel, or other implant grade metallic material, in an open-cell configuration. It should be appreciated that in other embodiments the stent 38 may be formed from a polymeric material and may be formed in, for example, a Z-stent configuration. In the illustrative embodiment, the outer surface 42 of the stent 38 is covered with low-profile polyester, ePTFE, or other nonporous covering material 44 that prevents fluid from passing through the outer surface 42. However, it should be appreciated that the stent 38 may be covered with standard polyester, ePTFE or other nonporous materials.

As shown in FIG. 17, the stent 38 of the balloon-expandable frame 34 has a diameter 46. As described in greater detail below, the balloon-expandable frame 34 is expandable during implantation from an unexpanded diameter (not shown) to the expanded diameter 46. In the illustrative embodiment, the expanded diameter 46 is equal to approximately 26 mm when the frame 34 is expanded. In other embodiments, the expanded diameter may be greater than or less than 26 mm depending on, for example, the patient's anatomy. In the illustrative embodiment, the diameter 46 is oversized relative to the diameter of the aortic annulus 210 such that an interference fit is created between the stent 38 and the annulus 210 when the transcatheter valve component 312 is implanted.

The balloon-expandable frame 34 is attached to a self-expanding frame 350. In the illustrative embodiment, the distal end 52 of the balloon-expandable frame 34 is secured to the proximal end 54 of the frame 350 by stitching or sewing the frames 34, 350 together, thereby forming the frame 26 of the transcatheter valve component 312. It should be appreciated that in other embodiments the frames 34, 350 may be secured together via welding or other fasteners. The frames 34, 350 may also be formed as a single, monolithic frame.

As shown in FIG. 17, the self-expanding frame 350 has a generally hourglass shape and is formed from a metallic material, such as, nitinol, stainless steel, or other implant grade metallic material. It should be appreciated that in other embodiments the frame 350 may be formed from a polymeric material. The frame 350 includes an inwardly tapered proximal section 360, an outwardly tapered middle section 62, and an elongated distal section 64. The section 360 includes the proximal end 54 of the frame 350 and has a distal end 66 connected to the proximal end 68 of the outwardly tapered middle section 62. The section 360 tapers inwardly between the ends 54, 66 from approximately 26 mm at the end 54 to approximately 22 mm at the end 66. In the illustrative embodiment, the proximal section 360 has a length 70 of approximately 15 mm.

The outwardly tapered middle section 62 of the self-expanding frame 350 has the proximal end 68 and a distal end 72 connected to the proximal end 74 of the elongated distal section 64. The section 62 tapers outwardly from a diameter of approximately 22 mm at the end 68 to a diameter of approximately 28 mm at the end 72. In the illustrative embodiment, the middle section 62 has a length 76 of approximately 10 mm. In other embodiments, the dimensions of the section 62 may vary depending on, for example, the patient's anatomy.

The elongated distal section 64 of the self-expanding frame 350 extends distally from the proximal end 74 to the distal end 30 of the valve component 312. In the illustrative embodiment, the section 64 has a length 78 that is greater than the combined length of the tapered sections 60, 62. In one particular non-limiting example, the length 78 of the elongated distal section 64 is approximately 30 mm and has a diameter 80 of approximately 34 mm. In other embodiments, the dimensions of the section 64 may vary depending on, for example, the patient's anatomy. In one exemplary embodiment, the distal section 64 may taper between the proximal end 74 and the distal end 30.

As shown in FIG. 3, the proximal section 360 of the self-expanding frame 350 is formed in an open-cell stent configuration, and each of the sections 62, 64 is formed in a Z-stent configuration. It should be appreciated that in other embodiments the sections 360, 62, 64 may be formed in a single configuration, including the open-cell stent configuration, mesh-like stent configuration, or Z-stent configuration. The sections 60, 62, 64 may also be formed as a single monolithic component.

As shown in FIG. 17, the outer surface 314 of the proximal section 360 of the frame 350 is uncovered such that fluid is permitted to pass through the openings 318. The outer surface 316 of the sections 62, 64 are covered with low profile polyester, ePTFE, or other nonporous covering material 84 such that fluid is prevented from passing through the surface 320. The outer surface 320 of the valve component 312 may also be covered with low-profile Dacron or other synthetic material. The uncovered, open cell stent section 360 is configured to allow for coronary artery perfusion. The covered sections 62, 64 serve to stabilize the valve component 312 against the aorta 18 and provide a docking station to ascending aortic extensions or fenestrated/branch arch grafts. The covered sections 62, 64 would also permit endograft extension of the valve component 312 for suitable type B aneurysms without dilation of the sinutubular junction.

The delivery of the transcatheter valve component 312 may begin by gaining access to the left ventricle across the native aortic valve. An ascending aortogram may be performed to locate the right and left coronary arteries. An over the wire introducer system, including a guidewire, is used to introduce the valve component 312 into the aorta 18. After the guidewire has been placed into the left ventricle 204 via the iliofemoral, subclavian, or carotid vessels, the valve component 312 may be delivered through the common femoral artery and passed across the native aortic valve 202.

After performing an angiogram to delineate the location of the coronary arteries 182, the valve component 312 is released by unsheathing the delivery system, thereby permitting expansion of the self-expanding frame 350, as shown in FIGS. 18-19.

The balloon-expandable frame 34 may be now deployed by inflating the balloon within the delivery system. This deploys the frame 34 to the predetermined expanded diameter 46 and advances the frame 34 into engagement with the aortic annulus 210, thereby sealing the aortic annulus 210 such that fluid is permitted to pass from the left ventricle 204 only through the valve 32 and the valve 32 is positioned in the aortic annulus 210 proximal to the coronary arteries 182, as shown in FIGS. 18-19. The openings 318 of the uncovered section 360 of the valve component 312 permit blood flow to the coronary arteries 182 for promote circulation. It should be appreciated that the deployment of the valve component 312 may be performed during rapid ventricular pacing (RVP).

Figure 20:
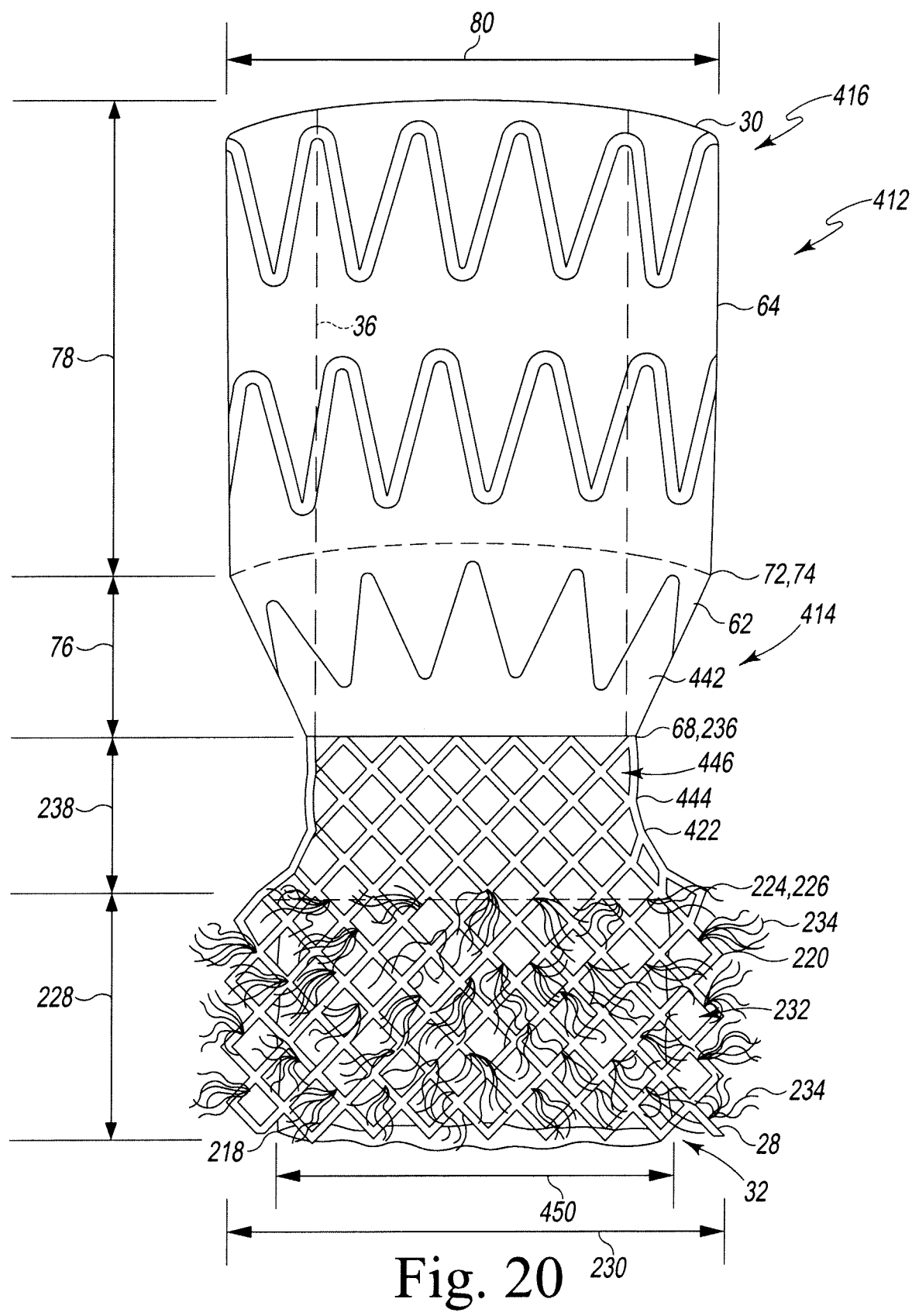
FIG. 20 is another embodiment of a transcatheter valve device similar to the proximal prosthetic component of FIG. 8.
Figure 21:
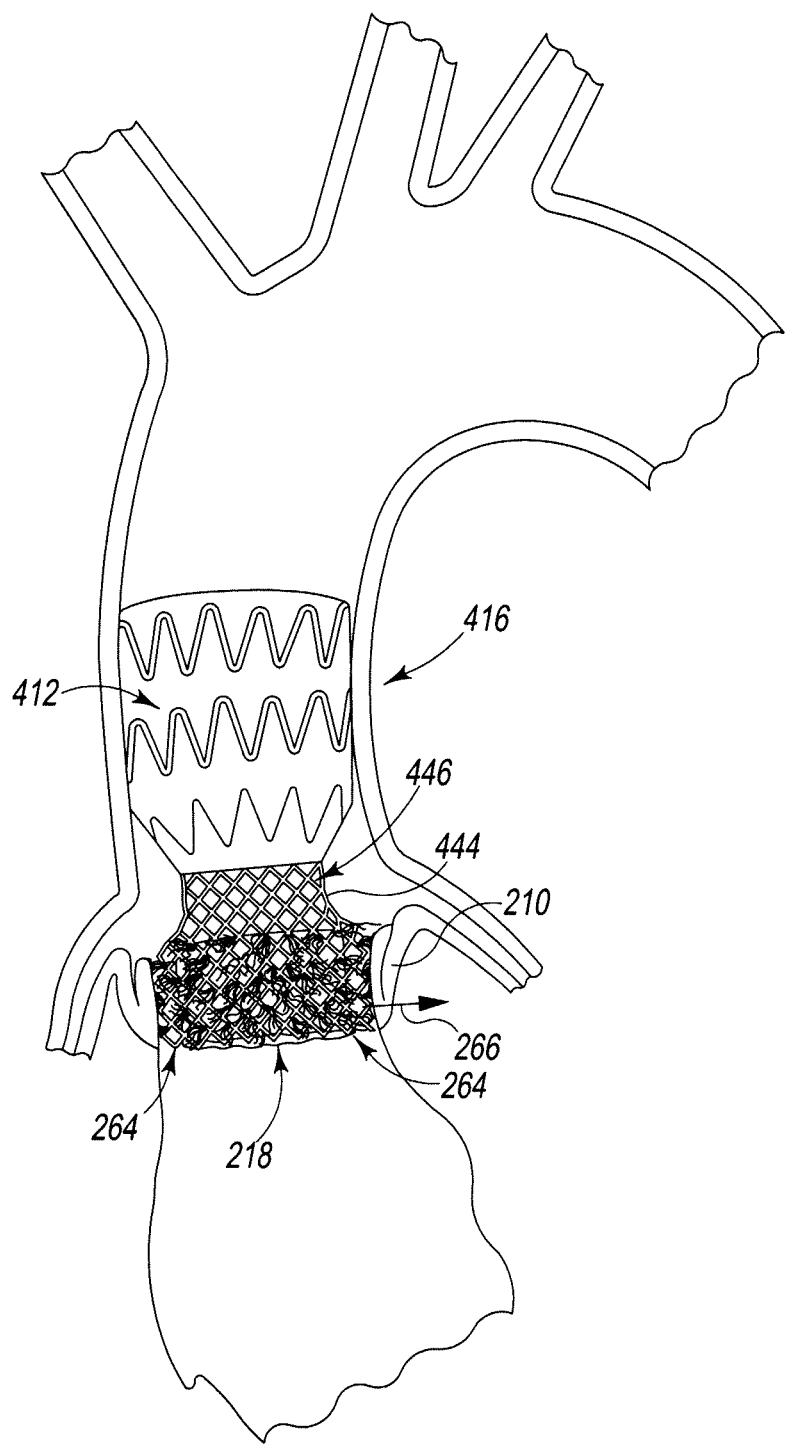
FIGS. 21-22 are partial cutaway views of the aorta with the transcatheter valve of FIG. 20 implanted therein.
Figure 22:
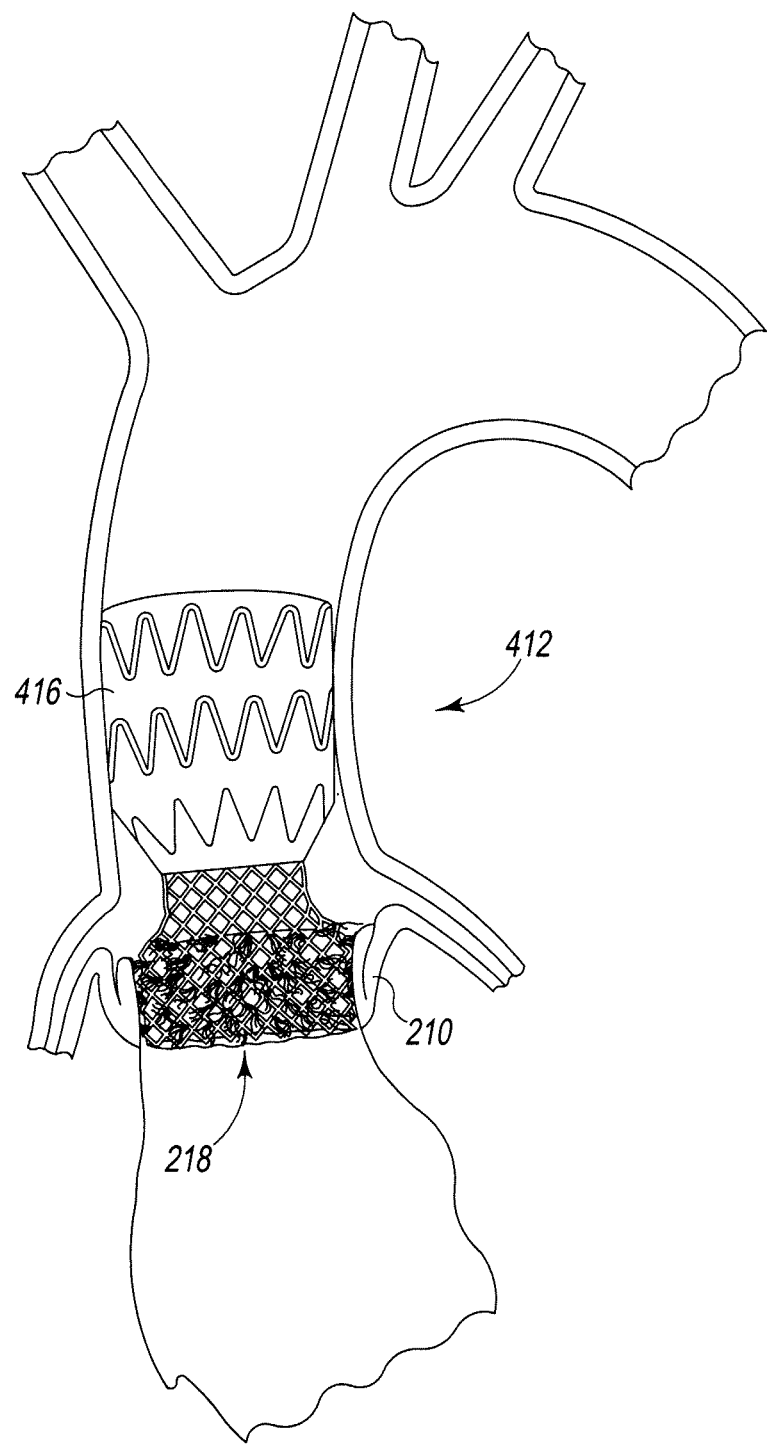

Referring now to FIGS. 20-22, another embodiment of a transcatheter valve component (hereinafter valve component 412) is shown. Some features of the embodiment illustrated in FIGS. 20-22 are substantially similar to those described above in reference to the proximal component 212 of FIGS. 8-16. Such features are designated in FIGS. 20-22 with the same reference numbers as those used in FIGS. 8-16. Similar to the proximal component 212 of FIGS. 8-16, the valve component 412 includes a dual-frame 414 that extends from a proximal end 28 to a distal end 30. The frame 414 is attached to a valve 32 (shown in phantom), which is positioned at the proximal end 28 of the component 412. In the illustrative embodiment, the valve 32 is configured as a bicuspid valve. When the valve component 412 is implanted into the patient's aorta 16, the valve 32 replaces the aortic valve and permits fluid (i.e., blood) to selectively pass from the heart and into a passageway 36 extending through the valve component 412.

The dual-frame 414 includes a self-expanding outer frame 416 and a balloon-expandable inner frame 218 that is secured to the self-expanding outer frame 416 and houses the valve 32. Referring now to FIG. 9, the self-expanding outer frame 416 has a generally hourglass shape and is formed from a metallic material, such as, nitinol, stainless steel, or other implant grade metallic material. It should be appreciated that in other embodiments the outer frame 416 may be formed from a polymeric material. The outer frame 416 includes an elongated proximal section 220, an inwardly tapered section 422, an outwardly tapered middle section 62, and an elongated distal section 64.

The elongated proximal section 220 of the outer frame 416 includes the proximal end 28 of the component 412 and has a distal end 224 connected to a proximal end 226 of the inwardly tapered section 222. The proximal section 220 is embodied as a tubular stent. It should be appreciated that in other embodiments the section 220 may be shaped as a prism, cone, or other geometric shape depending on the patient's anatomy.

In the illustrative embodiment, the proximal section 220 has a length 228 that is equal to approximately 15 mm. The proximal section 220 also has a diameter 230 of approximately 32 mm. It should be appreciated that in other embodiments the dimensions of the frame 416 may vary according to the anatomy of the patient. In the illustrative embodiment, the diameter 230 is oversized relative to the diameter of the aortic annulus 210 such that an interference fit is created between the proximal section 220 and the annulus 210 when the valve component 412 is implanted, as described in greater detail below. As shown in FIG. 9, the proximal section 220 defines a passageway 232 in the outer frame 416.

In the illustrative embodiment, collagen fibers 234 are attached to the proximal section 220 to aid in preventing paravalvular leaks and migration of the valve component 412 within the aortic walls. The fibers 234 extend outwardly from the proximal section 220 and inwardly into the passageway 232. It should be appreciated that in other embodiments the outer frame 216 may be covered with hydrogel or other sealing materials. In other embodiments, a plurality of barbs or hooks may be attached to the proximal section 220. The hooks may be configured to further engage the tissue of the aorta and inhibit or prevent migration of the device 10.

The inwardly tapered section 422 of the outer frame 416 includes the proximal end 226 and a distal end 236 connected to the proximal end 68 of the outwardly tapered middle section 62. The section 422 tapers inwardly between the ends 226, 236 from approximately 32 mm at the end 226 to approximately 22 mm at the end 236. In the illustrative embodiment, the inwardly tapered section 422 has a length 238 of approximately 10 mm.

The outwardly tapered middle section 62 of the self-expanding frame 416 has the proximal end 68 and a distal end 72 connected to the proximal end 74 of the elongated distal section 64. The section 62 tapers outwardly from a diameter of approximately 22 mm at the end 68 to a diameter of approximately 28 mm at the end 72. In the illustrative embodiment, the middle section 62 has a length 76 of approximately 10 mm. In other embodiments, the dimensions of the section 62 may vary depending on, for example, the patient's anatomy.

The elongated distal section 64 of the self-expanding frame 416 extends distally from the proximal end 74 to the distal end 30 of the component 412. In the illustrative embodiment, the section 64 has a length 78 that is greater than the combined length of the tapered sections 60, 62. In one particular non-limiting example, the length 78 of the elongated distal section 64 is approximately 30 mm and has a diameter 80 of approximately 34 mm. In other embodiments, the dimensions of the section 64 may vary depending on, for example, the patient's anatomy. In one exemplary embodiment, the distal section 64 may taper between the proximal end 74 and the distal end 30.

As shown in FIG. 20, each of the proximal section 220 and the inwardly tapered section 422 of the self-expanding frame 416 is formed in an open-cell stent configuration, and each of the sections 62, 64 is formed in a Z-stent configuration. It should be appreciated that in other embodiments the sections 62, 64, 220, 422 may be formed in a single configuration, including the open-cell stent configuration, mesh-like stent configuration, or Z-stent configuration. The sections 62, 64, 220, 422 may also be formed as a single monolithic component. The outer surfaces 440 of the sections 62, 64 are covered with low profile polyester, ePTFE, or other nonporous covering material 442 such that fluid is prevented from passing through the surface 440. The outer surface 444 of the section 422 is uncovered such that fluid is permitted to pass through openings 446 defined in the surface 444. The uncovered, open cell section 422 is configured to allow for coronary artery perfusion. The covered sections 62, 64 serve to stabilize the valve component 412 against the aorta 18 and provide a docking station to ascending aortic extensions or fenestrated/branch arch grafts.

As described above, the outer frame 416 of the dual-frame 414 is secured to a balloon-expandable inner frame 218, which is positioned in the passageway 232 and houses the valve 32. As described above, the balloon-expandable frame 218 is expandable during implantation from an unexpanded diameter 450 to the expanded diameter (not shown).

To deploy the valve component 412, a stiff wire is passed through the aortic valve 202 into the left ventricle 204. The delivery system for the valve component 412 is then passed through the valve 202. When the delivery system is in position, the valve component 412 is released by unsheathing the system, thereby permitting expansion of the self-expanding frame 416. The proximal section 220 of the frame 416 expands into engagement with the aortic annulus 210, thereby creating an interference fit between the frame 416 and the annulus 210 and stabilizing the valve component 412 in place. As shown in FIG. 21, the inner frame 218 is initially unexpanded within the outer frame 416. The inner frame 218 may be deployed by expanding the balloon assembly. Expansion of the balloon-expandable inner frame 218 engages the inner frame 218 with the outer frame 416 and compresses the collagen fiber/hydrogel coated proximal section 220 of the outer frame 416 against the aortic annulus 210.

As shown in FIG. 22, the combined engagement of the frames 218, 416 seals the annulus 210 and the paravalvular areas, and thus, prevents paravalvular leakage. As such, fluid is permitted to pass from the left ventricle 204 only through the valve 32 of the component 412. The openings 446 of the uncovered section 422 of the valve component 412 permit blood flow to the coronary arteries 182 for promote circulation.

It should be appreciated that the design of components 12, 14, 212 and the transcatheter valves 312, 412 has intentionally taken into account the potential failure modes and allows for correction of any such failure modes. For example, with respect to components 12, 14, 212, paravalvular leaks may be corrected. More specifically, with respect to a paravalvular leak (type Ia endoleak), leakage around the valve 32 would act as a type Ia endoleak. The trapdoors 86 in components 12, 312 would allow for coil embolization of the area of the leak. Two trapdoors at 180 degree location would allow access to the entire area above the aortic annulus. Since the coronary arteries 182 are protected by the conduits 22 in the distal component 14, coil embolization of this area would not compromise the coronary blood flow. Coil embolization of paravalvular leaks are already being performed clinically after heart valve surgery if there are additional leaks around the valve.

Aortic insufficiency (AI) after implantation may also be corrected. Significant AI has been documented in up to 17% of patients after transcatheter valve implantation. Except heavy annular calcification, the tricuspid morphology of the current valves and the ovoid shape of the aortic annulus can cause malcoaptation of the valve leaflets causing AI. The bicuspid valve nature of the designs discussed herein potentially eliminates the problem with malcoaptation and AI secondary to that.

Structural valve degeneration may also be corrected. More specifically, the bicuspid valve design allows for placement of another transcatheter valve across the first device without compromising valvular flow area.

Coronary insufficiency may also be corrected. The Cabrol endo-conduits 22 in conjunction with the tapered section 128 of component 14 ensure uninterrupted coronary blood flow. By first deploying the component 14, the surgeon will be able to work through the Cabrol conduits 22 and using standard catheters and guidewires to cannulate the right and left coronary arteries. Stents 24 are deployed from the coronary arteries into the Cabrol conduits 22. Deployment the component 12 or component 212 may be delayed until coronary blood flow is secured. The tapered design will mitigate the risk of compression of the coronary stents between the device 10 and the aortic wall.

For the transcatheter valves 312, 412, paravalvular leaks may also be corrected in that the open cell midsections 360, 422 of the valve allow the cannulation and stenting of the coronary arteries with potential coil embolization of the leak after the protection of the coronary artery if necessary.

Structural valve degeneration in the transcatheter valves 312, 412 may be corrected in that the bicuspid valve design permit for placement of another transcatheter valve across the first device without compromising valvular flow area.

The dual frame component may also take the form of other transcatheter valvular replacement devices such as, for example, prosthetic mitral and tricuspid valves. The dual frame component may also be used to enhance sealing zones of endovascular devices to treat abdominal and thoracic aneurysms, and in applications to treat peripheral vascular disease.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

What is claimed:

1. A transcatheter valve assembly, comprising:
a main body that defines a stent frame and a graft material covering at least a portion thereof, wherein the graft material is at a distal end of the transcatheter valve assembly;
a medial portion that defines a gridded, uncovered surface that is positioned about the coronary arteries when the valve assembly is deployed;
a valve housing at the proximal end of the transcatheter valve assembly, the valve housing including a prosthetic valve element therein and the prosthetic valve element being positioned at the proximal end of the transcatheter valve assembly,
wherein the gridded, uncovered surface is positioned between the graft material and the valve housing.

2. The transcatheter valve assembly of claim 1, wherein the graft material covers an entire length of the stent frame.

3. The transcatheter valve assembly of claim 1, wherein the medial portion defines a tapering or reduced diameter to provide clearance external to the valve assembly.

4. The transcather valve assembly of claim 1, wherein the valve housing defines a wire frame having a graft material covering thereon.

5. The transcatheter valve assembly of claim 1, wherein the main body is self-expanding.

6. The transcatheter valve assembly of claim 1, wherein the main body is self-expanding in response to unsheathing of the main body.

7. The transcatheter valve assembly of claim 1, wherein the transcatheter valve assembly is deployed through an access artery.

8. The transcatheter valve assembly of claim 1, wherein a plurality of fibers is attached to the valve housing.

9. The transcatheter valve assembly of claim 1, wherein the valve housing is covered with at least one of a collagen or hydrogel.

10. The transcatheter valve assembly of claim 1, wherein the prosthetic valve element is one of a bicuspid valve and a tricuspid valve.

11. The transcather valve assembly of claim 1, wherein the valve assembly is configured for engaging a second stent component positioned in the aorta.

12. The transcatheter valve assembly of claim 1, wherein the valve assembly is offset from the main body by the medial portion.

13. A method comprising:
accessing an access artery of a patient with a transcatheter valve assembly that comprises a main body that defines a stent frame and a graft material covering at least a portion thereof, wherein the graft material is at a distal end of the transcatheter valve assembly, a medial portion that defines a gridded, uncovered surface, and a valve housing at a proximal end of the transcatheter valve assembly, the valve housing including a prosthetic valve element therein and the prosthetic valve element being positioned at the proximal end of the transcatheter valve assembly, wherein the gridded, uncovered surface is positioned between the graft material and the valve housing;
endovascularly deploying the transcatheter valve assembly through the access artery,
positioning the gridded, uncovered surface about the coronary arteries;
expanding the transcatheter valve assembly into engagement with the aorta of the patient.

14. The method of claim 13, wherein the graft material covers an entire length of the stent frame.

15. The method of claim 13, wherein the medial portion defines a tapering or reduced diameter to provide clearance external to the valve assembly.

16. The method of claim 13, wherein the valve housing defines a wire frame having a graft material covering thereon.

17. The method of claim 13, wherein the main body is self-expanding.

18. The method of claim 13, wherein the main body is self-expanding in response to unsheathing of the main body.

19. The method of claim 13, further comprising deploying a second stent component with the transcather valve assembly.

20. The method of claim 13, wherein the valve assembly is offset from the main body by the medial portion.

21. A transcatheter valve assembly, comprising:
a main body that defines a stent frame and a graft material covering at least a portion thereof, wherein the graft material is at a distal end of the transcatheter valve assembly;
a medial portion that defines a gridded, uncovered surface that is positioned about the coronary arteries when the valve assembly is deployed;
a valve housing at the proximal end of the transcatheter valve assembly, the valve housing including a prosthetic valve element therein and the prosthetic valve element being positioned at the proximal end of the transcatheter valve assembly;
wherein the gridded, uncovered surface is positioned between the graft material and the valve housing,
wherein the main body, medial portion, and valve housing are integrally formed such that deployment of the main body, medial portion, and valve housing is accomplished simultaneously.

* * * * *